US011986459B2

(12) United States Patent
Baker et al.

(10) Patent No.: US 11,986,459 B2
(45) Date of Patent: May 21, 2024

(54) METHODS FOR THE TREATMENT OF MYCOBACTERIUM INFECTIONS

(71) Applicant: University of South Florida, Tampa, FL (US)

(72) Inventors: Bill J. Baker, Temple Terrace, FL (US); Kyle Rohde, Orlando, FL (US); Bingjie Yang, Temple Terrace, FL (US); Marisa Fuse, Winter Springs, FL (US)

(73) Assignees: University of South Florida, Tampa, FL (US); UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 147 days.

(21) Appl. No.: 17/713,576

(22) Filed: Apr. 5, 2022

(65) Prior Publication Data

US 2022/0226284 A1    Jul. 21, 2022

Related U.S. Application Data

(63) Continuation of application No. 17/375,403, filed on Jul. 14, 2021, now abandoned.

(60) Provisional application No. 63/051,476, filed on Jul. 14, 2020.

(51) Int. Cl.

| | |
|---|---|
| *A61K 31/12* | (2006.01) |
| *A61K 31/133* | (2006.01) |
| *A61K 31/145* | (2006.01) |
| *A61K 31/192* | (2006.01) |
| *A61K 31/235* | (2006.01) |
| *A61K 31/343* | (2006.01) |
| *A61K 31/352* | (2006.01) |
| *A61K 31/365* | (2006.01) |
| *A61K 31/366* | (2006.01) |
| *A61K 31/4015* | (2006.01) |
| *A61K 31/4045* | (2006.01) |
| *A61K 31/44* | (2006.01) |
| *A61K 31/4409* | (2006.01) |
| *A61K 31/454* | (2006.01) |
| *A61K 31/472* | (2006.01) |
| *A61K 31/496* | (2006.01) |
| *A61K 31/498* | (2006.01) |
| *A61K 31/505* | (2006.01) |
| *A61K 31/7036* | (2006.01) |
| *A61P 31/06* | (2006.01) |

(52) U.S. Cl.
CPC ............ *A61K 31/366* (2013.01); *A61K 31/12* (2013.01); *A61K 31/133* (2013.01); *A61K 31/145* (2013.01); *A61K 31/192* (2013.01); *A61K 31/235* (2013.01); *A61K 31/343* (2013.01); *A61K 31/352* (2013.01); *A61K 31/365* (2013.01); *A61K 31/4015* (2013.01); *A61K 31/4045* (2013.01); *A61K 31/44* (2013.01); *A61K 31/4409* (2013.01); *A61K 31/454* (2013.01); *A61K 31/472* (2013.01); *A61K 31/496* (2013.01); *A61K 31/498* (2013.01); *A61K 31/505* (2013.01); *A61K 31/7036* (2013.01); *A61P 31/06* (2018.01)

(58) Field of Classification Search
CPC ................................ A61K 31/12; A61P 31/06
See application file for complete search history.

(56) References Cited

U.S. PATENT DOCUMENTS

2019/0321368 A1    10/2019  Song

OTHER PUBLICATIONS

Hemtasin, Chulida, et al. "Bioactive azaphilones from the fungus *Penicillium multicolor* CM01." Phytochemistry Letters 16 (2016): 56-60.

Cheng, Ya-Juan, et al. "Discovery of (3-Benzyl-5-hydroxyphenyl) carbamates as new antitubercular agents with potent in vitro and in vivo efficacy." Molecules 24.10 (2019): 2021.

Arai, Noriko, et al. "Isochromophilones III-VI, inhibitors of acyl-CoA: cholesterol acyltransferase produced by Penicillium multicolor FO-3216." The Journal of Antibiotics 48.7 (1995): 696-702.

Asif, M. An overview on fluoroquinolone drugs for the treatment of tubercular infection. J. Med. Chem. Sci. 2019, 2, 172-176. https://doi.org/10.26655/jmchemsci.2019.8.7.

Birkinshaw, J. H.; Kalyanpur, M. G.; Stickings, C. E. Studies in the biochemistry of microorganisms. 113. pencolide, a nitrogen-containing metabolite of penicillium multicolor grigorieva25 manilova and poradielova. *Biochem. J.* 1963, 86, 237-243.

Björn, Bode. H.; Barbara, B.; Regina, H.; Axel, Z. Big effects from small changes: possible ways to explore nature's chemical diversity. ChemBioChem. 2002, 3, 619-627. https://doi.org/10.1002/1439-7633(20020703)3:7<619::AID-CBIC619>3.0.CO;2-9.

Cheng, Z.; Pan, J.-H.; Tang, W.; Chen, Q.; Lin, Y. Biodiversity and biotechnological potential of mangrove-associated fungi. J. For. Res. 2009, 20, 63-72. https://doi.org/10.1007/s11676-009-0012-4.

Churchyard, G. J.; Swindells, S. Controlling Latent TB tuberculosis infection in high burden countries: a neglected strategy to end TB. PLoS Med. 2019, 16, e1002787. https://doi.org/10.1371/journal.pmed.1002787.

Demers, D. H., et al., Exploitation of mangrove endophytic fungi for infectious disease drug discovery. Mar. Drugs. 2018, 16, 376. https://doi.org/10.3390/md16100376.

(Continued)

*Primary Examiner* — James D. Anderson
(74) *Attorney, Agent, or Firm* — Meunier Carlin & Curfman LLC

(57) ABSTRACT

The present disclosure provides methods for the treatment of infections with *Mycobacterium* such as *tuberculosis* or leprosy.

10 Claims, 8 Drawing Sheets

(56) References Cited

OTHER PUBLICATIONS

Ding, B.; Wang, Z.; Huang, X.; Liu, Y.; Chen, W.; She, Z. Bioactive α-pyrone meroterpenoids from mangrove endophytic fungus *Penicillium* sp. Nat. Prod. Res. 2016, 30, 2805-2812. https://doi.org/10.1080/14786419.2016.1164702.
Elkington, P; Tebruegge, M; Mansour S, Tuberculosis: an infection-initiated autoimmune disease? Trends. Immunol., 2016, 37, 815-818.
Epigenetic modification increases susceptibility to obesity and predicts fatty liver https://medicalxpress.com/news/2016-05-epigenetic-modification-susceptibility-obesityfatty.html (accessed Jan. 6, 2020).
Frisvad, J. C.; Smedsgaard, J.; Larsen, T. O.; Samson, R. A. Mycotoxins, drugs and other extrolites produced by species in *Penicillium* subgenus *Penicillium*. Stud. Mycol., 2004, 49, 201-241.
Gu, B.-B.; wu, Y.; Tang, J.; Jiao, W.; Li, L.; Sun, F.; Wang, S.-P.; Yang, F.; Lin, H.-W. Azaphilone and isocoumarin derivatives from the sponge-derived fungus *Eupenicillium* sp. 6A-9. Tetrahedron. Lett. 2018, 59, 3345-3348. https://doi.org/10.1016/j.tetlet.2018.06.057.
Guo, Qingfeng, et al. "A new azaphilone from the entomopathogenic fungus *Hypocrella* sp." Natural product research 29.21 (2015): 2000-2006.
Khan, MK, Islam, MN, Ferdous, J, Alam, MM. An overview on epidemiology of tuberculosis. Mymensingh Med. J. 2019, 28, 259-266. https://europepmc.org/article/med/30755580 (accessed Jan. 6, 2020).
Kiazyk, S.; Ball, T. Latent tuberculosis infection: an overview. Can. Commun. Dis. Rep. 2017, 43, 62-66.
Kumaresan, V. Occurrence, Distribution and bioactive potential of mangrove fungal endophytes: an appraisal. KAVAKA, 2017, 48, 44-49.
Lee, M., et al., Delamanid, Linezolid, Levofloxacin, and pyrazinamide for the treatment of patients with fluoroquinolone-sensitive multidrug-resistant tuberculosis (treatment shortening of MDR-TB using existing and new drugs, MDR-END): study protocol for a phase II/III, multicenter, randomized, open-label clinical trial Trials 2019, 20, 57. https://doi.org/10.1186/s13063-018-3053-1.
Lucas, E. M. F.; Castro, M. C. M. de; Takahashi, J. A. Antimicrobial properties of sclerotiorin, isochromophilone VI and pencolide, metabolites from a brazilian cerrado isolate of penicillium sclerotiorum van beyma. Braz. J. Microbiol. 2007, 38, 785-789. https://doi.org/10.1590/S1517-83822007000400036.
Mangrove Species Profiles https://www.floridamuseum.ufl.edu/southflorida/habitats/mangroves/species/ (accessed Jan. 7, 2020).
Matsuzaki, K.; Tahara, H.; Inokoshi, J.; Tanaka, H.; Masuma, R.; Omura, S. New brominated and halogen-less derivatives and structure-activity relationship of azaphilones inhibiting gp120-cd4 binding. J. Antibiot. 1998, 51, 1004-1011. https://doi.org/10.7164/antibiotics.51.1004.
Michael, Adam P., et al. "Isochromophilone IX, a novel GABA-containing metabolite isolated from a cultured fungus, *Penicillium* sp." Australian journal of chemistry 56.1 (2003): 13-15.
Son, Sangkeun, et al. "Structures and biological activities of azaphilones produced by *Penicillium* sp. KCB11A109 from a ginseng field." Phytochemistry 122 (2016): 154-164.
Strobel GA, Daisy B, Castillo U, Harper J. 2004. Natural products from endophytic microorganisms. J Nat Prod, 67: 257-268.
Szyf M. 2015. Prospects for the development of epigenetic drugs for CNS conditions. Nature Reviews Drug Discovery 14, 461-474.
Tabuchi, Hiroyasu, and Akitami Ichihara. "Structures and stereochemistries of new compounds related to alternaric acid." Journal of the Chemical Society, Perkin Transactions 1 1 (1994): 125-133.
Tresner, H. D.; Hayes, J. A. Sodium chloride tolerance of terrestrial fungi. Appl. Microbiol. 1971, 22, 210-213.
Tsang, C. A.; Shah, N.; Armstrong, L. R.; Marks, S. M. Eligibility for a shorter treatment regimen for multidrug-resistant tuberculosis in the united states, 2011-2016. Clin. Infect. Dis. 2020, 70, 907-916 https://doi.org/10.1093/cid/ciz263.
Wang, X.; Sena Filho, J. G.; Hoover, A. R.; King, J. B.; Ellis, T. K.; Powell, D. R.; Cichewicz, R. H. Chemical epigenetics alters the secondary metabolite composition of guttate excreted by an atlantic-forest-soil-derived penicillium citreonigrum. J. Nat. Prod. 2010, 73, 942-948. https://doi.org/10.1021/np100142h.
Weishampel PA, Bedford BL. 2006. Wetland dicots and monocots differ in colonization by arbuscular mycorrhizal fungi and dark septate endophytes. Mycorrhiza, 16(7): 495-502.
Wen, S.; Fan, W.; Guo, H.; Huang, C.; Yan, Z.; Long, Y. Two new secondary metabolites from the mangrove endophytic fungus *Pleosporales* Sp. SK7. Nat. Prod. Res. 2019, 0, 1-7. https://doi.org/10.1080/14786419.2019.1598993.
Zhang, L.; Niaz, S. I.; Khan, D.; Wang, Z.; Zhu, Y.; Zhou, H.; Lin, Y.; Li, J.; Liu, L. Induction of diverse bioactive secondary metabolites from the mangrove endophytic fungus *Trichoderma* sp. (strain 307) by co-cultivation with acinetobacter johnsonii (strain B2). Mar. Drugs. 2017, 15, 35. https://doi.org/10.3390/md15020035.

METHODS FOR THE TREATMENT OF MYCOBACTERIUM INFECTIONS

CROSS-REFERENCE TO RELATED APPLICATIONS

This application is a continuation of U.S. application Ser. No. 17/375,403, filed Jul. 14, 2021, which claims the benefit of priority to U.S. Provisional Application No. 63/051,476, filed Jul. 14, 2020, the disclosure of each of which is incorporated herein by reference in its entirety.

STATEMENT REGARDING FEDERALLY SPONSORED RESEARCH

This invention was made with government support under Grant Nos. AI103673 and AI103715 awarded by the National Institute of Allergy and Infection Diseases of the National Institute of Health. The government has certain rights in the invention.

FIELD OF THE INVENTION

The present disclosure is directed to methods for treating *Mycobacterium* infections such as *tuberculosis* or leprosy.

BACKGROUND

*tuberculosis* is a common and often deadly infectious caused by *Mycobacterium tuberculosis* bacteria. *tuberculosis* generally affects the lungs, but can also affect other parts of the body. Most infections are latent (i.e. do not have symptoms), but about 10% of latent *tuberculosis* infections progress to active disease which can kill about half of those affected if left untreated. The class symptoms of *tuberculosis* are a chronic cough with blood-containing sputum, fever, night sweats, and weight loss. Infection of other organ can lead to a wider range of symptoms.

Treatment for *tuberculosis* is difficult, requiring long-term administration of antibiotics. For treatment of active *tuberculosis*, a patient is typically administered isoniazid (with pyridoxal phosphate), rifampin, pyrazinamide, and ethambutol daily for two months, followed by administration of isoniazid and rifampin daily for a further four months. For latent *tuberculosis*, the standard treatment is administration of isoniazid alone for three months or three months of weekly isoniazide/rifapentine combination therapy. Antibiotic resistance is a growing problem for *tuberculosis*, with treatment regimens for resistant strains requiring the administration of stronger drugs over longer time periods. Some strains of *tuberculosis* are completely resistant to all currently used drugs.

Thus, there is a clear need for new therapeutic methods for the treatment of *Mycobacterium* infections.

SUMMARY

In accordance with the purposes of the disclosed materials and methods, as embodied and broadly described herein, the disclosed subject matter, in one aspect, relates to methods for the treatment of infections and other disorders caused by *Mycobacterium*, for example *tuberculosis* or leprosy.

Thus, in one aspect, a method of treating an infection with a *Mycobacterium* in a subject is provided comprising administering a therapeutically effective amount of one or more compounds selected from:

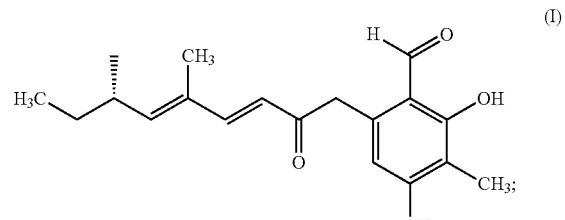

(I)

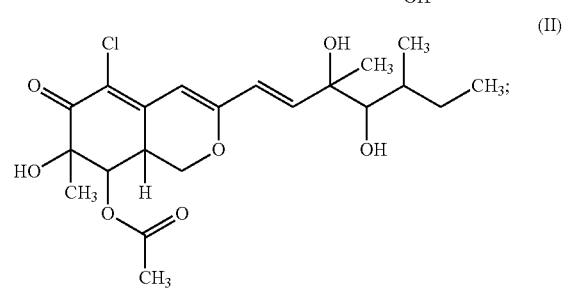

(II)

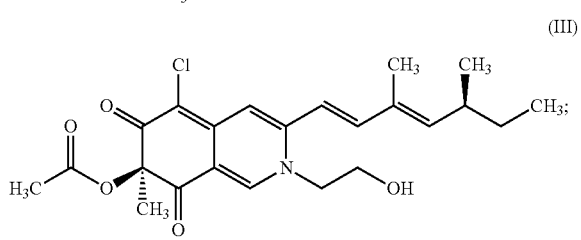

(III)

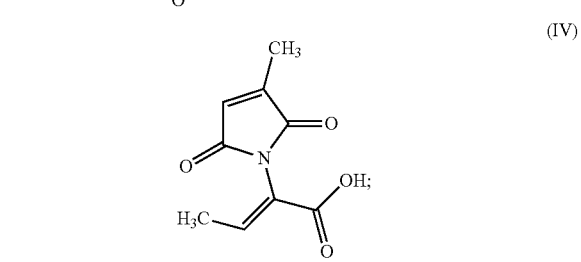

(IV)

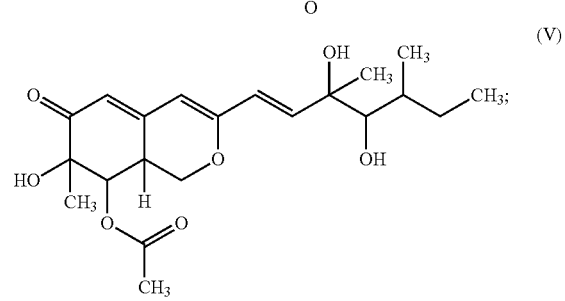

(V)

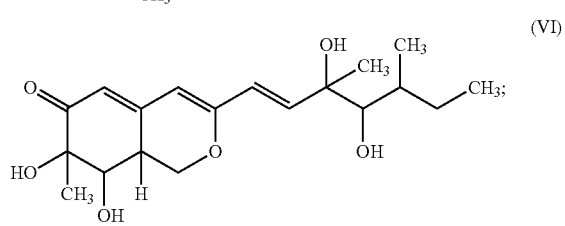

(VI)

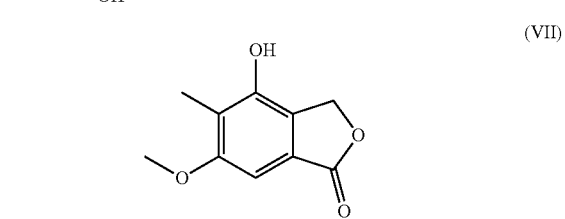

(VII)

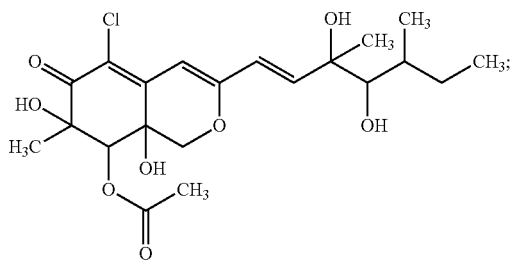

(VIII)

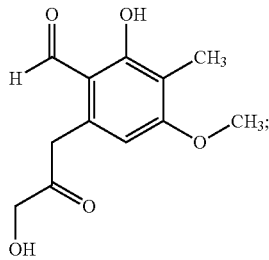

(IX)

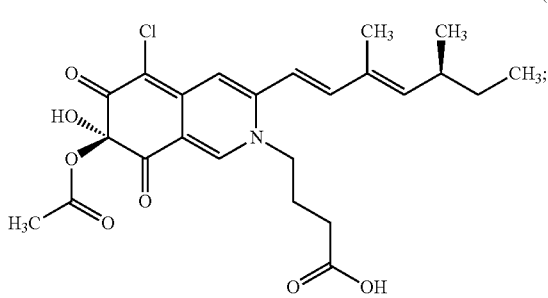

(X)

or pharmaceutically acceptable salts thereof, prodrugs, or esters thereof.

In some embodiments, the one or more compounds, or pharmaceutically acceptable salts, prodrugs, or esters thereof, are administered in combination with a pharmaceutically acceptable carrier to form a pharmaceutical composition.

In some embodiments, the infection comprises *tuberculosis*. In some embodiments, the infection is caused by *Mycobacterium africanum, Mycobacterium bovis, Mycobacterium canetti, Mycobacterium caprae, Mycobacterium microti, Mycobacterium mungi, Mycobacterium orygis, Mycobacterium pinnipedii, Mycobacterium suricattae*, or *Mycobacterium tuberculosis*.

In some embodiments, the infection comprises leprosy. In some embodiments, the infection is caused by *Mycobacterium leprae* or *Mycobacterium lepromatosis*.

In some embodiments, the infection is caused by *Mycobacterium avium, Mycobacterium avium* paratuberculosis, *Mycobacterium avium silvaticum, Mycobacterium avium hominissuis, Mycobacterium colombiense, Mycobacterium indicus pranii, Mycobacterium intracellulare, Mycobacterium ulcerans, Mycobacterium marinum, Mycobacterium kansasii, Mycobacterium abscessus, Mycobacterium chelonae, Mycobacterium fortuitum, mycobacterium terrae, Mycobacterium xenopi*, and *Mycobacterium simiae*.

In some embodiments, the one or more compounds are administered in combination or alternation with one or more additional therapeutic agents, for example ethambutol, isoniazid, pyrazinamide, rifampicin, streptomycin, acedapsone, clofazimine, dapsone, desoxyfructo-serotonin, ethionamide, rifapentine, sulfameter, thalidomide, or combinations thereof.

In some embodiments, the subject is a human.

In another aspect, a method for killing one or more *Mycobacterium* cells is provided comprising administering an effective amount of one or more compounds selected from Formula I, Formula II, Formula III, Formula IV, Formula V, Formula VI, Formula VII, Formula VIII, Formula IX, Formula X, or a pharmaceutically acceptable salt, prodrug, or ester thereof.

In yet another aspect, a method for inhibiting the growth of one or more *Mycobacterium* cells is provided comprising administering an effective amount of one or more compounds selected from Formula I, Formula II, Formula III, Formula IV, Formula V, Formula VI, Formula VII, Formula VIII, Formula IX, Formula X, or a pharmaceutically acceptable salt, prodrug, or ester thereof.

Additional advantages will be set forth in the description that follows, and in part will be obvious from the description, or may be learned by practice of the aspects described below. The advantages described below will be realized and attained by means of the elements and combinations particularly pointed out in the appended claims. The foregoing and other features will be come apparent from the following detailed description of several embodiments which proceed with reference to the accompanying drawings.

DETAILED DESCRIPTION

Figure 1:
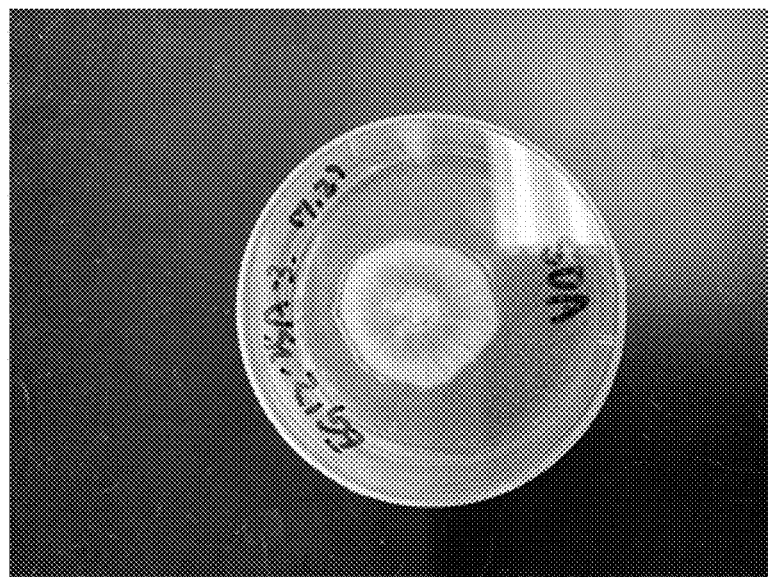
FIG. 1 shows an isolation plate for fungal strain EG12-25A-3 as further described in the examples.

The following description of the disclosure is provided as an enable teaching of the disclosure in its best, currently known embodiments. To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are part of the present disclosure. Thus, the following description is provided as illustrative of the principles of the present disclosure and not in limitation thereof.

Definitions

Unless defined otherwise, all technical and scientific terms used herein have the same meaning as commonly understood to one of ordinary skill in the art to which this invention belongs. The following definitions are provided for the full understanding of terms used in the specification.

As used in the specification and claims, the singular form "a", "an", and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration but are undetectable or detectable at negligible amounts in distal parts of the subject's body. Administration includes self-administration and the administration by another.

As used here, the terms "beneficial agent" and "active agent" are used interchangeably herein to refer to a chemical compound or composition that has a beneficial biological effect. Beneficial biological effects include both therapeutic effects, i.e., treatment of a disorder or other undesirable physiological condition, and prophylactic effects, i.e., prevention of a disorder or other undesirable physiological condition. The terms also encompass pharmaceutically acceptable, pharmacologically active derivatives of beneficial agents specifically mentioned herein, including, but not limited to, salts, esters, amides, prodrugs, active metabolites, isomers, fragments, analogs, and the like. When the terms "beneficial agent" or "active agent" are used, then, or when a particular agent is specifically identified, it is to be understood that the term includes the agent per se as well as pharmaceutically acceptable, pharmacologically active salts, esters, amides, prodrugs, conjugates, active metabolites, isomers, fragments, analogs, etc.

As used herein, the terms "treating" or "treatment" of a subject includes the administration of a drug to a subject with the purpose of preventing, curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, prevention of the occurrence of symptoms and/or their underlying cause, and improvement or remediation of damage.

As used herein, the term "preventing" a disorder or unwanted physiological event in a subject refers specifically to the prevention of the occurrence of symptoms and/or their underlying cause, wherein the subject may or may not exhibit heightened susceptibility to the disorder or event.

By the term "effective amount" of a therapeutic agent is meant a nontoxic but sufficient amount of a beneficial agent to provide the desired effect. The amount of beneficial agent that is "effective" will vary from subject to subject, depending on the age and general condition of the subject, the particular beneficial agent or agents, and the like. Thus, it is not always possible to specify an exact "effective amount". However, an appropriate "effective" amount in any subject case may be determined by one of ordinary skill in the art using routine experimentation. Also, as used herein, and unless specifically stated otherwise, an "effective amount" of a beneficial can also refer to an amount covering both therapeutically effective amounts and prophylactically effective amounts.

An "effective amount" of a drug necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

As used herein, a "therapeutically effective amount" of a therapeutic agent refers to an amount that is effective to achieve a desired therapeutic result, and a "prophylactically effective amount" of a therapeutic agent refers to an amount that is effective to prevent an unwanted physiological condition. Therapeutically effective and prophylactically effective amounts of a given therapeutic agent will typically vary with respect to factors such as the type and severity of the disorder or disease being treated and the age, gender, and weight of the subject. The term "therapeutically effective amount" can also refer to an amount of a therapeutic agent, or a rate of delivery of a therapeutic agent (e.g., amount over time), effective to facilitate a desired therapeutic effect. The precise desired therapeutic effect will vary according to the condition to be treated, the tolerance of the subject, the drug and/or drug formulation to be administered (e.g., the potency of the therapeutic agent (drug), the concentration of drug in the formulation, and the like), and a variety of other factors that are appreciated by those of ordinary skill in the art.

As used herein, the term "pharmaceutically acceptable" component can refer to a component that is not biologically or otherwise undesirable, i.e., the component may be incorporated into a pharmaceutical formulation of the invention and administered to a subject as described herein without causing any significant undesirable biological effects or interacting in a deleterious manner with any of the other components of the formulation in which it is contained. When the term "pharmaceutically acceptable" is used to refer to an excipient, it is generally implied that the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disuifonic, oxalic, isethionic, HOOC—$(CH2)n$-COOH where n is 0-4, and the like, or using a different acid that produces the same counterion. Lists of additional suitable salts may be found, e.g., in Remington's Pharmaceutical Sciences, 17th ed., Mack Publishing Company, Easton, Pa., p. 1418 (1985).

Also, as used herein, the term "pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

As used herein, the term "subject" or "host" can refer to living organisms such as mammals, including, but not limited to, humans, livestock, dogs, cats, and other mammals. Administration of the therapeutic agents can be carried out at dosages and for periods of time effective for treatment of a subject. In some embodiments, the subject is a human.

The compounds described herein include enantiomers, mixtures of enantiomers, diastereomers, tautomers, racemates and other isomers, such as rotamers, as if each is specifically described, unless otherwise indicated or otherwise excluded by context. It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form. Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, and methods, examples of which are illustrated in the accompanying Examples and Figures.

Methods of Treatment

As discussed above, the compounds described herein can be used to treat or prevent a disease, disorder, or condition in a patient in need thereof that is the result of an infection by a *Mycobacterium*, for example *Mycobacterium tuberculosis, Mycobacterium leprae* or *Mycobacterium lepromatosis*. In some embodiments, treatment refers to partial or complete alleviation, amelioration, relief, inhibition, delaying onset, or reducing severity and/or incidence of the disease, disorder, or condition in the patient.

Disclosed herein are methods of treating an infection with a *Mycobacterium* in a subject by administering a therapeutically effective amount of one or more compounds selected from Formula I, Formula II, Formula III, Formula IV, Formula V, Formula VI, Formula VII, Formula VIII, Formula IX, or Formula X, or pharmaceutically acceptable salts, prodrugs, or esters thereof, optionally in a pharmaceutically acceptable carrier to form a pharmaceutical composition. In one embodiment, a method for the treatment of an infection with *Mycobacterium tuberculosis* in a subject is provided comprising administering a therapeutically effective amount of one or more compounds selected from Formula I, Formula II, Formula III, Formula IV, Formula V, Formula VI, Formula VII, or a pharmaceutically acceptable salt, prodrug, or ester thereof, optionally in a pharmaceutically acceptable carrier to form a pharmaceutical composition.

In one embodiment, a method is provided for the treatment of *tuberculosis* in a subject comprising administering an effective amount of a compound of Formula I:

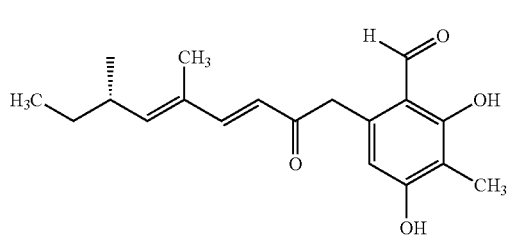

(I)

or a pharmaceutically acceptable salt, prodrug, or ester thereof.

In another embodiment, a method is provided for the treatment of *tuberculosis* in a subject comprising administering an effective amount of a compound of Formula II:

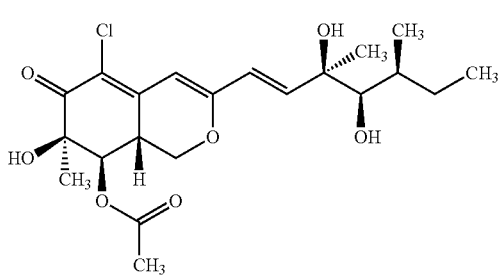

(II)

Or a pharmaceutically acceptable salt, prodrug, or ester thereof.

In one embodiment, the compound of Formula II as used in the methods described herein is a compound of Formula II-a:

(II-a)

or a pharmaceutically acceptable salt, prodrug, or ester thereof.

In another embodiment, the compound of Formula II as used in the method described herein is a compound of Formula II-b:

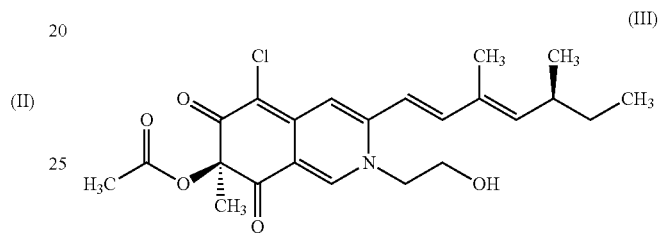

(II-b)

In another embodiment, a method is provided for the treatment of *tuberculosis* in a subject comprising administering an effective amount of a compound of Formula III:

(III)

or a pharmaceutically acceptable salt, prodrug, or ester thereof.

In another embodiment, a method is provided for the treatment of *tuberculosis* in a subject comprising administering an effective amount of a compound of Formula IV:

(IV)

or a pharmaceutically acceptable salt, prodrug, or ester thereof.

In another embodiment, a method is provided for the treatment of *tuberculosis* in a subject comprising administering an effective amount of a compound of Formula V:

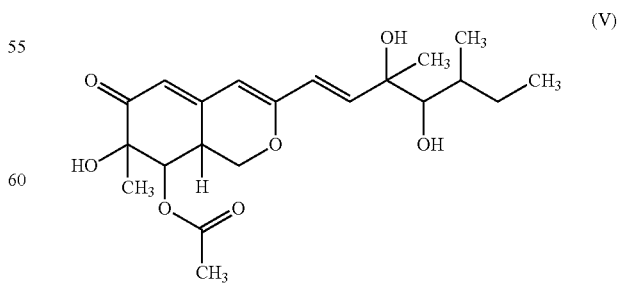

(V)

or a pharmaceutically acceptable salt, prodrug, or ester thereof.

In one embodiment, the compound of Formula V as used herein is a compound of Formula V-a:

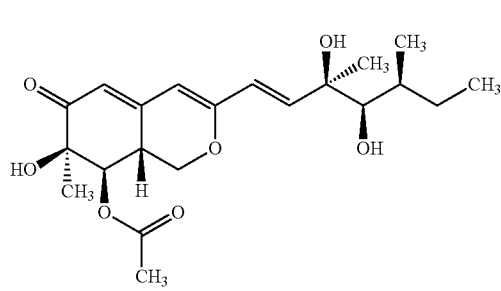

(V-a)

or a pharmaceutically acceptable salt, prodrug, or ester thereof.

In another embodiment, a method is provided for the treatment of *tuberculosis* in a subject comprising administering an effective amount of a compound of Formula VI:

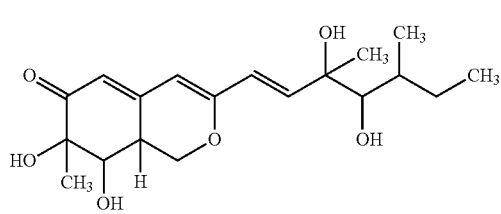

(VI)

or a pharmaceutically acceptable salt, prodrug, or ester thereof.

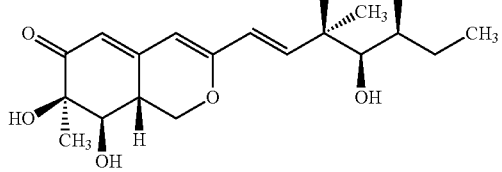

(VI-a)

or a pharmaceutically acceptable salt, prodrug, or ester thereof.

In another embodiment, a method is provided for the treatment of *tuberculosis* in a subject comprising administering an effective amount of a compound of Formula VII:

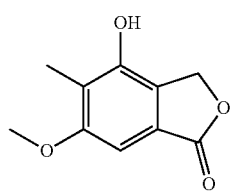

(VII)

or a pharmaceutically acceptable salt, prodrug, or ester thereof.

In another embodiment, a method is provided for the treatment of *tuberculosis* in a subject comprising administering an effective amount of a compound of Formula VIII:

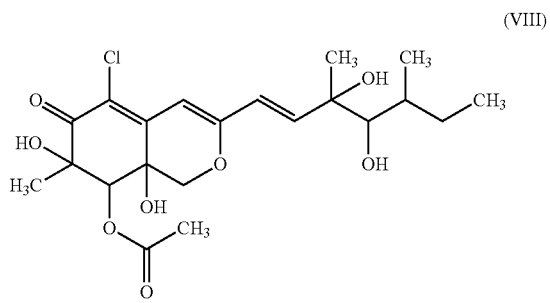 [SMILES: CCC(C)C(O)C(C)(O)/C=C/C1=CC2=C(Cl)C(=O)C(C)(O)C(OC(C)=O)C2(O)CO1]

(VIII)

or a pharmaceutically acceptable salt, prodrug, or ester thereof.

In another embodiment, a method is provided for the treatment of *tuberculosis* in a subject comprising administering an effective amount of a compound of Formula IX:

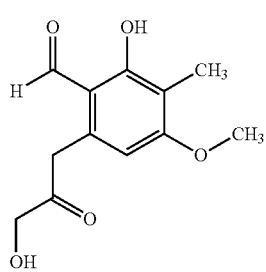

(IX)

or a pharmaceutically acceptable salt, prodrug, or ester thereof.

In another embodiment, a method is provided for the treatment of *tuberculosis* in a subject comprising administering an effective amount of a compound of Formula X:

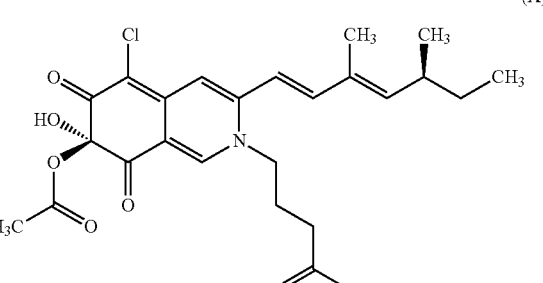

(X)

or a pharmaceutically acceptable salt, prodrug, or ester thereof.

In another embodiment, a method is provided for the treatment of an infection caused by *Mycobacterium leprae* or *Mycobacterium lepromatosis* in a subject comprising administering an effective amount of one or more compounds selected from Formula I, Formula II, Formula III, Formula IV, Formula V, Formula VI, Formula VII, Formula VIII, Formula IX, or Formula X, or pharmaceutically acceptable salts, prodrugs, or esters thereof. In another embodiment, a method is provided for the treatment of leprosy in a subject comprising administering an effective amount of one or more compounds selected from Formula I, Formula II, Formula III, Formula IV, Formula V, Formula VI, Formula VII, Formula VIII, Formula IX, or Formula X, or pharmaceutically acceptable salts, prodrugs, or esters thereof.

In another embodiment, a method is provided for the killing of *Mycobacterium* cells comprising administering an effective amount of one or more compounds selected from Formula I, Formula II, Formula III, Formula IV, Formula V, Formula VI, Formula VII, Formula VIII, Formula IX, or Formula X, or a pharmaceutically acceptable salt, prodrug, or ester thereof. In another embodiment, a method is provided for the killing of *Mycobacterium tuberculosis* cells comprising administering an effective amount of one or more compounds selected from Formula I, Formula II, Formula III, Formula IV, Formula V, Formula VI, Formula VII, Formula VIII, Formula IX, or Formula X, or a pharmaceutically acceptable salt, prodrug, or ester thereof.

In another embodiment, a method is provided for inhibiting the growth of *Mycobacterium* cells comprising administering an effective amount one or more compounds selected from Formula I, Formula II, Formula III, Formula IV, Formula V, Formula VI, Formula VII, Formula VIII, Formula IX, or Formula X, or a pharmaceutically acceptable salt, prodrug, or ester thereof.

Representative examples of *Mycobacterium* that may be treated by the methods described herein include, but are not limited to: *M. africanum, M. bovis, M. bovis* BCG, *M. canetti, M. caprae, M. microti, M. mungi, M. oryngis, M. pinnipedii, M. suricattae, M. tuberculosis, M. avium, M. avium paratuberculosis, M. avium silvaticum, M. avium "hominissuis", M. colombiense, M. indicus pranii, M. intracellulare, M. asiatium, M. gordonae, M. gastri, M. kansasii, M. hiberniae, M. icosiumassiliensis, M. nonchromogenicum, M. terrae, M. Ovate, M. ulcerans, M. pseudoshottsii, M. shottsii, M. florentinum, M. genavense, M. heidelbergense, M. interjectum, M. kubicae, M. lentiflavum, M. montefiorense, M. palustre, M. parascrofulaceum, M. simiae, M. triplex, M. arabiense, M. aromaticivorans, M. aquaticum, M. bacteremicum, M. bohemicum, M. botniense, M. branderi, M. celatum, M. chimaera, M. conspicuum, M. cookii, M. doricum, M. farcinogenes, M. haemophilum, M. heckeshornense, M. intracellulare, M. lacus, M. leprae, M. lepromatosis, M. liflandii, M. llatzerense, M. malmoense, M. marinum, M. neoaurum, M. monacense, M. murale, M. nebraskense, M. saskatchewanense, M. sediminis, M. scrofulaceum, M. shimoidei, M. szulgai, M. talmoniae, M. tusciae, M. xenopi, M. yongonense, M. intermedium, M. abscessus, M. bolletii, M. massiliense, M. chelonae, M. immunogenum, M. stephanolepidis, M. boenickei, M. brisbanense, M. cosmeticum, M. fortuitum, M. fortuitum* subsp. *acetamidolyticum, M. houstonense, M. mageritense, M. neworleansense, M. peregrinum, M. porcinum, M. senegalense, M. septicum, M. aubagnese, M. mucogenium, M. phocaicum, M. austroafricanum, M diernhoferi, M. frederiksbergense, M. hodleri, M. neoaurum, M. parafortuitum, M. aurum, M. vaccae, M. chitae, M. fallax, M. agri, M. aicheinse, M. alvei, M. arupense, M. barrassiae, M. brumae, M. canariasense, M. chubuense, M. conceptionense, M. confulentis, M. duvalii, M. elephantis, M. flavascens, M. gadium, M. gilvum, M. hassiacum, M. holsaticum, M. iranicum, M. komossense, M. madagascariense, M. massihpolynesiensis, M. moriokaense, M. obuense, M. phlei, M. psychrotolerans, M. pulveris, M. pyrenivorans, M. smegmatis, M. goodii, M. w olinskyi, M sphagni, M. thermoresistibile, M. vanbaalenii,* *M. arosiense, M. aubagnense, M. chlorophenolicum, M. fluoroanthenivorans, M. kumamatonense, M. novocastrense, M. parmense, M. poriferae, M. Rhodesia, M. seoulense,* and *M. tokaiense.*

In another embodiment, a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, is provided for the treatment of infection caused by a *Mycobacterium*. In another embodiment, a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, is provided for the treatment of *tuberculosis* in a subject. In another embodiment, a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, is provided for the treatment of leprosy in a subject.

In another embodiment, use a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, in an effective amount in the treatment of a subject with a *Mycobacterium* infection is provided. In another embodiment, use a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, in an effective amount in the treatment of a subject with *tuberculosis* is provided. In another embodiment, use a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, in an effective amount in the treatment of a subject with leprosy is provided.

In another embodiment, use a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, in the manufacture of a medicament for the treatment of a *Mycobacterium* infection in a subject is provided. In another embodiment, use a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, in the manufacture of a medicament for the treatment of a *Mycobacterium* infection in a subject is provided. In another embodiment, use a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, in the manufacture of a medicament for the treatment of *tuberculosis* in a subject is provided. In another embodiment, use a compound of Formula I, Formula II, Formula III, Formula IV, Formula V, Formula VI, Formula VII, Formula VIII, Formula IX, or Formula X, or a pharmaceutically acceptable salt, prodrug, or ester thereof, or combinations thereof, in the manufacture of a medicament for the treatment of leprosy in a subject is provided.

The present disclosure also includes compounds as used in the methods herein with at least one desired isotopic substitution of an atom, at an amount above the natural abundance of the isotope, i.e., enriched.

Examples of isotopes that can be incorporated into compounds of the present disclosure include isotopes of hydrogen, carbon, nitrogen, oxygen, and chlorine, such as $^2$H, $^3$H, $^{11}$C, $^{13}$C, $^{15}$N, $^{17}$O, $^{18}$O, and $^{36}$Cl, respectively. In one embodiment, isotopically labeled compounds can be used in metabolic studies (with $^{14}$C), reaction kinetic studies (with, for example $^2$H or $^3$H), detection or imaging techniques, such as positron emission tomography (PET) or single-photon emission computed tomography (SPECT) including drug and substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed herein by substituting a readily available isotopically labeled reagent for a non-isotopically labeled reagent.

By way of general example and without limitation, isotopes of hydrogen, for example deuterium ($^2$H) and tritium ($^3$H) may optionally be used anywhere in described structures that achieves the desired result. Alternatively or in addition, isotopes of carbon, e.g., $^{13}$C and $^{14}$C, may be used. In one embodiment, the isotopic substitution is replacing hydrogen with a deuterium at one or more locations on the molecule to improve the performance of the molecule as a drug, for example, the pharmacodynamics, pharmacokinetics, biodistribution, half-life, stability, AUC, Tmax, Cmax, etc. For example, the deuterium can be bound to carbon in allocation of bond breakage during metabolism (an alpha-deuterium kinetic isotope effect) or next to or near the site of bond breakage (a beta-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95, or 99% or more enriched in an isotope at any location of interest. In some embodiments, deuterium is 80, 85, 90, 95, or 99% enriched at a desired location. Unless otherwise stated, the enrichment at any point is above natural abundance, and in an embodiment is enough to alter a detectable property of the compounds as a drug in a human.

The compounds as used in the present disclosure may form a solvate with solvents (including water). Therefore, in one embodiment, the invention includes use of a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a disclosed compound and water. Pharmaceutically acceptable solvates in accordance with the invention include those wherein the solvent of crystallization may be isotopically substituted, e.g., D$_2$O, d6-acetone, or d6-DMSO. A solvate can be in a liquid or solid form.

A "prodrug" as used herein means a compound which when administered to a host in vivo is converted into a parent drug. As used herein, the term "parent drug" means any of the presently described compounds herein. Prodrugs can be used to achieve any desired effect, including to enhance properties of the parent drug or to improve the pharmaceutic or pharmacokinetic properties of the parent, including to increase the half-life of the drug in vivo. Prodrug strategies provide choices in modulating the conditions for in vivo generation of the parent drug. Non-limiting examples of prodrug strategies include covalent attachment of removable groups, or removable portions of groups, for example, but not limited to, acylating, phosphorylation, phosphonylation, phosphoramidate derivatives, amidation, reduction, oxidation, esterification, alkylation, other carboxy derivatives, sulfoxy or sulfone derivatives, carbonylation, or anhydrides, among others. In certain embodiments, the prodrug renders the parent compound more lipophilic. In certain embodiments, a prodrug can be provided that has several prodrug moieties in a linear, branched, or cyclic manner. For example, non-limiting embodiments include the use of a divalent linker moiety such as a dicarboxylic acid, amino acid, diamine, hydroxycarboxylic acid, hydroxyamine, di-hydroxy compound, or other compound that has at least two functional groups that can link the parent compound with another prodrug moiety, and is typically biodegradable in vivo. In some embodiments, 2, 3, 4, or 5 prodrug biodegradable moieties are covalently bound in a sequence, branched, or cyclic fashion to the parent compound. Non-limiting examples of prodrugs according to the present disclosure are formed with: a carboxylic acid on the parent drug and a hydroxylated prodrug moiety to form an ester; a carboxylic acid on the parent drug and an amine prodrug to form an amide; an amino on the parent drug and a carboxylic acid prodrug moiety to form an amide; an amino on the parent drug and a sulfonic acid to form a sulfonamide; a sulfonic acid on the parent drug and an amino on the prodrug moiety to form a sulfonamide; a hydroxyl group on the parent drug and a carboxylic acid on the prodrug moiety to form an ester; a hydroxyl on the parent drug and a hydroxylated prodrug moiety to form an ester; a phosphonate on the parent drug and a hydroxylated prodrug moiety to form a phosphonate ester; a phosphoric acid on the parent drug and a hydroxylated prodrug moiety to form a phosphate ester; a hydroxyl on the parent drug and a phosphonate on the prodrug to form a phosphonate ester; a hydroxyl on the parent drug and a phosphoric acid prodrug moiety to form a phosphate ester; a carboxylic acid on the parent drug and a prodrug of the structure HO—(CH$_2$)$_2$—O—(C$_{2-24}$ alkyl) to form an ester; a carboxylic acid on the parent drug and a prodrug of the structure HO—(CH$_2$)$_2$—S—(C$_{2-24}$ alkyl) to form a thioester; a hydroxyl on the parent drug and a prodrug of the structure HO—(CH$_2$)$_2$—O—(C$_{2-24}$ alkyl) to form an ether; a hydroxyl on the parent drug and a prodrug of the structure HO—(CH$_2$)$_2$—O—(C$_{2-24}$ alkyl) to form an thioether; and a carboxylic acid, oxime, hydrazide, hydrazine, amine or hydroxyl on the parent compound and a prodrug moiety that is a biodegradable polymer or oligomer including but not limited to polylactic acid, polylactide-co-glycolide, polyglycolide, polyethylene glycol, polyanhydride, polyester, polyamide, or a peptide.

In some embodiments, a prodrug is provided by attaching a natural or non-natural amino acid to an appropriate functional moiety on the parent compound, for example, oxygen, nitrogen, or sulfur, and typically oxygen or nitrogen, usually in a manner such that the amino acid is cleaved in vivo to provide the parent drug. The amino acid can be used alone or covalently linked (straight, branched or cyclic) to one or more other prodrug moieties to modify the parent drug to achieve the desired performance, such as increased half-life, lipophilicity, or other drug delivery or pharmacokinetic properties. The amino acid can be any compound with an amino group and a carboxylic acid, which includes an aliphatic amino acid, alkyl amino acid, aromatic amino acid, heteroaliphatic amino acid, heteroalkyl amino acid, heterocyclic amino acid, or heteroaryl amino acid.

Combination Therapies

In some embodiments, the compounds as used in the methods described herein can be administered in combination with other therapies. The compounds described herein can be administered simultaneously, sequentially, or at distinct time points as part of the same therapeutic regimen.

In some embodiments, the compounds as used in the methods described herein may be administered in combination or alternation with a nucleic acid inhibitor. In some embodiments, the compounds as used in the methods described herein may be administered in combination or alternation with a rifamycin, for example rifampicin, rifabutin, rifapentine, rifalazil, or combinations thereof. In some embodiments, the compounds as used in the methods described herein may be administered in combination or alternation with an antifolate or a dihydropteroate synthase inhibitor, for example dapsone, acedapsone, aldesulfone sodium, or combinations thereof. In some embodiments, the compounds as used in the methods described herein may be administered in combination or alternation with 4-aminosalicyclic acid or a salt thereof, for example calcium aminosalicylate or sodium aminosalicylate. In some embodiments, the compounds as used in the methods described herein may be administered in combination with a quinolone antibiotic, for example gatifloxacin, moxifloxacin, or combinations thereof.

In some embodiments, the compounds as used in the methods described herein may be administered in combination or alternation with a protein synthesis inhibitor. In some embodiments, the compounds as used in the methods described herein may be administered in combination or alternation with an aminoglycoside, for example amikacin, kanamycin, streptomycin, or combinations thereof. In some embodiments, the compounds as used in the methods described herein may be administered in combination or alternation with an oxazolidinone antibiotic, for example linezolid or sutezolid. In some embodiments, the compounds as used in the methods described herein may be administered in combination or alternation with a polypeptide antibiotic, for example capreomycin.

In some embodiments, the compounds as used in the methods described herein may be administered in combination or alternation with a cell envelope antibiotic. In some embodiments, the compounds as used in the methods described herein may be administered in combination or alternation with cycloserine. In some embodiments, the compounds as used in the methods described herein may be administered in combination or alternation with an antibiotic effective on the peptidoglycan layer, for example cycloserine. In some embodiments, the compounds as used in the methods described herein may be administered in combination or alternation with a compound effective on the arabinogalactan layer, for example an ethylenediamine/arabinosyltransferase inhibitor such as ethambutol, or SQ109. In some embodiments, the compounds as used in the methods described herein may be administered in combination or alternation with an antibiotic effective on the mycolic acid layer, for example hydrazides/mycolic acid synthase inhibitors such as isoniazid and methaniazide, thiocarbamides such as ethionamide, prothionamide, and thiocarlide, and thioacetazone. In some embodiments, the compounds as used in the methods described herein may be administered in combination or alternation with phenazide, pyrazine, isoxazole, bedaquiline, and metronidazole.

In some embodiments, the compounds as used in the *tuberculosis* treatment methods described herein may be administered in combination or alternation with ethambutol, isoniazid, pyrazinamide, rifampicin, streptomycin, or combinations thereof. In other embodiments, the compounds as used in the *tuberculosis* treatment methods described herein may be administered in combination or alternation with aminoglycoside antibiotics (e.g., amikacin or kanamycin), polypeptide antibiotics (e.g., capreomycin, viomycin, of enviomycin), fluoroquinolones (e.g., ciprofloxacin, levofloxacin, or moxifloxacin), thioamides (e.g., ethionamide or prothionamide), cycloserine, terizidone, or combinations thereof. In other embodiments, the compounds as used in the *tuberculosis* treatment methods described herein may be administered in combination or alternation with rifabutin, macrolide antibiotics (e.g., clarithromycin), linezolid, thiacetazone, thioridazine, arginine, vitamin D, or bedaquiline.

In some embodiments, the compounds as used in the leprosy treatment methods described herein may be administered in combination or alternation with acedapsone, clofazimine, dapsone, desoxyfructo-serotonin, diucifon, ethionamide, rifampicin, rifapentine, sulfameter, thalidomide, or combinations thereof.

Methods of Administration

The compounds as used in the methods described herein can be administered by any suitable method and technique presently or prospectively known to those skilled in the art. For example, the active components described herein can be formulated in a physiologically- or pharmaceutically-acceptable form and administered by any suitable route known in the art including, for example, oral and parenteral routes of administering. As used herein, the term "parenteral" includes subcutaneous, intradermal, intravenous, intramuscular, intraperitoneal, and intrasternal administration, such as by injection. Administration of the active components of their compositions can be a single administration, or at continuous and distinct intervals as can be readily determined by a person skilled in the art.

Compositions, as described herein, comprising an active compound and an excipient of some sort may be useful in a variety of medical and non-medical applications. For example, pharmaceutical compositions comprising an active compound and an excipient may be useful for the treatment or prevention of an infection with a *Mycobacterium*.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Exemplary excipients include, but are not limited to, any non-toxic, inert solid, semisolid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water;

isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), buccally, or as an oral or nasal spray. In some embodiments, the active compounds disclosed herein are administered topically.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid. Other preservatives include tocopherol, tocopherol acetate, deteroxime mesylate, cetrimide, butylated hydroxyanisol (BHA), butylated hydroxytoluene (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, chamomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacrylic acid/acrylamide copolymer, polyalkylene oxides such as polyethylene oxide, polypropylene oxide, poly(ethylene oxide-propylene oxide), and a Pluronic polymer, polyoxy ethylene (polyethylene glycol), polyanhydrides, polyvinylalcohol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly (meth) acrylic acid, and esters amide and hydroxy alkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxy vinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes. Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general, the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days.

A number of embodiments of the invention have been described. Nevertheless, it will be understood that various modification may be made without departing from the spirit and scope of the invention. Accordingly, other embodiments are within the scope of the following claims.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Chemical Investigation of Anti-*tuberculosis* Floridian Mangrove Endophytes

Introduction

Tuberculosis

*tuberculosis* (TB), caused by bacterium *Mycobacterium tuberculosis*, is a worldwide leading cause of death, resulting in 10 million cases globally in 2017 and more than 2 million deaths every year.[1,2,3] At the same time, latent TB infection is also counted in global *tuberculosis* epidemic. Around 1.7 billion people have latent infection from TB, while some of them may turn to active TB. For example, HIV positive patients have high risk of processing latent to active TB.[4] The conventional treatments for TB are unsatisfying because of low compliance and high costs.[5] Moreover, treatments are required for more complicated situations, such as the emergence of multidrug-resistant *tuberculosis* (MDR-TB). Currently the recommended treatment regimen for MDR-TB by the World Health Organization (WHO) is 9-12 months.[6] Newer treatments with shorter treatment regimen and higher efficacy are urgently needed to overcome the challenge created from multidrug-resistant and extensively drug-resistant *tuberculosis*.[7]

Mangroves and Endophyte Chemistry

Mangroves mainly can be found in the intertidal zone in the tropical and subtropical regions. In Florida, there are three mangrove species constituting the coastal ecosystem, including the Red Mangrove (*Rhizophora mangle*), Black Mangrove (*Avicennia germinans*) and White Mangrove (*Laguncularia racemosa*). Mangroves are considered transition zone between terrestrial and marine habitats, which makes the interface capable of having marine and terrestrial fungi co-existing.[8]

Mangrove fungi form the second largest ecological group of the marine fungi. Exposure to higher salt concentration makes the marine fungal growth conditions significantly harsh, which leads to potential diversity and bioactivity. Studies of these fungi demonstrated that most of them produce structurally new and bioactive secondary metabolites.[10] The bioactivities include anti-tumor, anti-biotic, and anti-virus.[10] For example, Wen isolated a new abscisic acid-type sesquiterpene (1'S, 2Z)-3-Methyl-5-(2,6,6-trimethyl-4-oxocyclohex-2-enyl)pent-2-enoicacid, a new asterric acid derivative methyl 2-(2-carboxy-4-hydroxy-6-methoxylphenoxy)-6-hydroxy-4-methylbenzoate and three known compounds asterric acid, methyl asterrate and methyl 3-chloroasterric acid from mangrove endophytic fungus *Pleosporales* sp. SK7.[11]

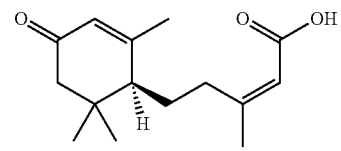

(1'S, 2Z)-3-Methyl-5-(2,6,6-trimethyl-4-oxocyclohex-2-enyl)
pent-2-enoic acid

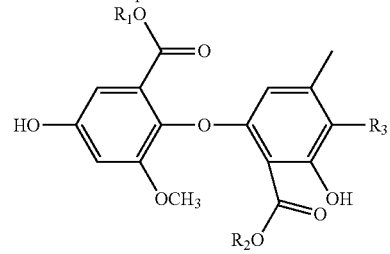

$R_1$ = H, $R_2$ = CH$_3$, $R_3$ = H, methyl 2-(2-carboxy-4-hydroxy-6-methoxylphenoxy)-6-hydroxy-4-methylbenzoate;
$R_1$ = CH$_3$, $R_2$ = H, $R_3$ = H, asterric acid;
$R_1$ = CH$_3$, $R_2$ = CH$_3$, $R_3$ = H, methyl asterrate;
$R_1$ = CH$_3$, $R_2$ = H, $R_3$ = Cl, methyl 3-chloroasterric acid Zhang, Niaz and Khan reported the isolation of two new sesquiterpenes microsphaeropsisin B and C, and two new de-O-methyllasiodiplodins, (3R,7R)-7-hydroxy-de-o-methyllasiodiplodin and (3R)-5-oxo-de-o-methyllasiodiplodin, along with a new natural product (3R)-7-oxo-de-O-methyllasiodiplodin, from the co-cultivation of a mangrove endophytic fungus *Trichoderma* sp. 307 and an aquatic pathogenic bacterium *Acinetobacter johnsonii* B2. Among these new secondary metabolites, (3R,7R)-7-hydroxy-de-O-methyllasiodiplodin and (3R)-5-oxo-de-O-methyllasiodiplodin exhibited α-glucosidase inhibition activity with IC$_{50}$ of 25.8 and 54.6 μM, which is significantly higher than the positive control acarbose with IC$_{50}$ of 703.8 μM.[12]

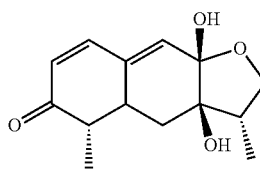

microsphaeropsisin B

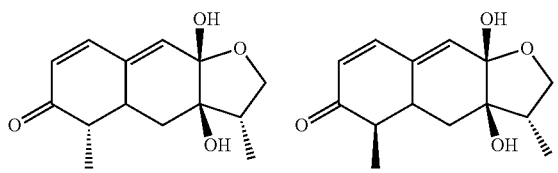

microsphaeropsisin C

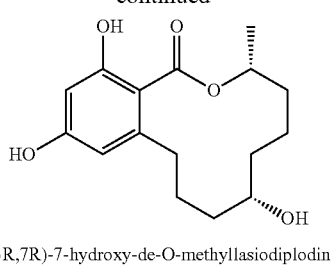

(3R,7R)-7-hydroxy-de-O-methyllasiodiplodin

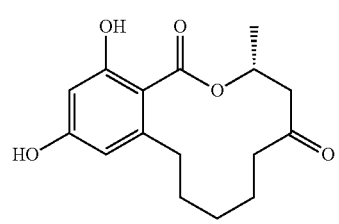

(3R)-5-oxo-de-O-methyllasiodiplodin

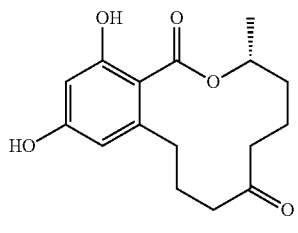

(3R)-7-oxo-de-O-methyllasiodiplodin

Ding and his colleagues worked on the marine fungus *Penicillium* sp. SK5GW1L and isolated a new α-pyrone meroterpenoid, 3-epiarigsugacin E and four known compounds from the same class, arisugacin D, arisugacin B, territrem C and terreulactone C. Arisugacin B, territrem C and terreulactone C exhibited activities against acetylcholinesterase (AchE) with $IC_{50}$ of 3.03, 0.23 and 0.028 μM.[13]

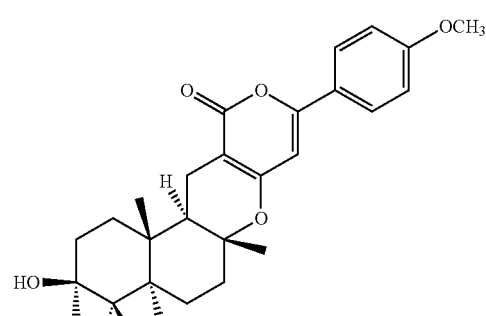

3-epiarigsugacin E

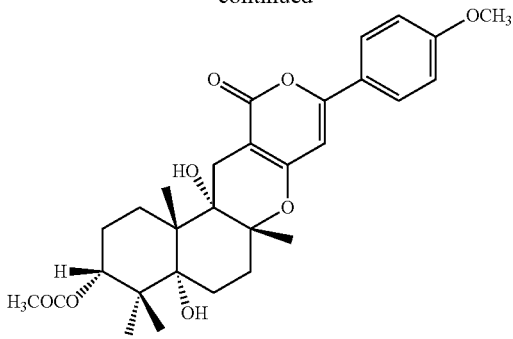

Arisugacin D

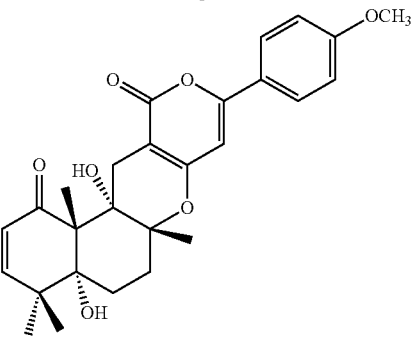

Arisugacin B

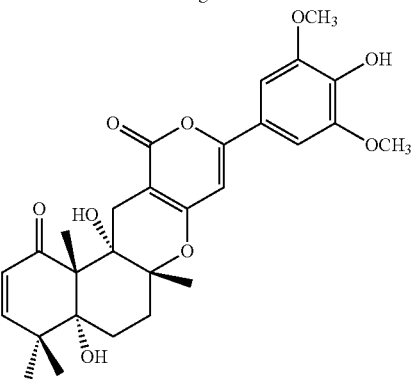

Territrem C

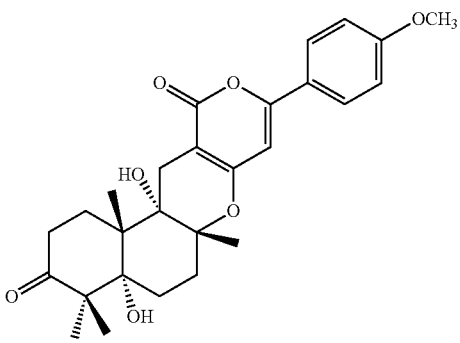

Terreulactone C

Epigenetic Modifications

Microorganisms, including fungi, produce diverse metabolites with a range of bioactivities that could be applied as the treatment of infectious diseases, different types of cancer, etc. However, there are many biosynthetic gene clusters (BGC) that stay silent or are expressed at very low levels in standard laboratory growing conditions.[14] Activation of cryptic and silent genes would reveal the great potential of microorganisms producing more specialized metabolites. Recently, more genomes have been sequenced, inspiring new approaches to explore novel microbial natural products.[15] Epigenetic modification is one of the developing methods. It can be only applied for eukaryotic gene expression since it is based on DNA and chromatin, which makes processes such as histone deacetylation and DNA methylation as a means to enhance expression.

Research Objectives

There is an urgent need for new and effective drugs to treat infectious diseases, including TB. Mangrove forests offer a diverse environment for the endophytic fungi to produce potential bioactive metabolites. It has been proved that mangrove endophytes have the potential to produce bioactive metabolites. However, Floridian mangroves have not been well-studied compared to the mangroves from other areas, for example Asia. At the same time, epigenetic modification is a tool to access potential bioactive compounds that are not translated and produced in regular growth conditions. Our goal is to discover new bioactive fungal metabolites against TB, with application of the epigenetic modification method.

Chemical Investigation of Epigenetically Modulated Red Mangrove Endophytes Selection and Growth of Bioactive Fungal Strains Mangrove tissues were collected from different environments within Florida, covering various microclimates. Collections sites include Courtney Campbell Causeway, Tampa, FL (CC); Coquina Beach, Sarasota, FL (CQ); Everglades City, FL (EG); Howard Frankland Bridge, Tampa, FL (HF); and Keys Marine Lab, Layton, FL (KML)).

High-throughput screening (HTS) against *Mycobacterium tuberculosis*, the ESKAPE panel of bacterial pathogens, *Leishmania donovani* and *Naegleria fowleri* was carried out for almost 2700 fungal strains isolated from mangrove collections. Dr. Kyle Rohde's lab in University of Central Florida (UCF) was carrying out the bioassay test against *Mycobacterium tuberculosis*. With epigenetic-modulated cultures and non-epigenetic-modulated (control) culture of each fungal strain, 8000 fungal extracts were produced and screened for their bioactivity. Among these extracts, 71 were specifically targeted to *Mycobacterium tuberculosis* (Mtb).[17]

Isolation and Characterization of Anti-*tuberculosis* Secondary Metabolites

Based on the results from the pilot HTS, fungal strains with significant bioactivity were selected to be cultured on a larger scale. One strain, EG12-25A-3 (EverGlades 2012 colony 25 from isolation plate with media type A and colony 3 from purification plate) (FIG. 1) was prioritized according to its anti-TB bioactivity. It exhibited 85% inhibition activity against *M. tuberculosis* and 48.2% inhibition activity against non-*tuberculosis Mycobacterium Mycobacterium abscessus* (Mab) in the DNA methyltransferase (DNMT) inhibitor-treated culture. Larger scale cultivation was applied to this fungal strain to produce more extract biomass, followed by chemical investigation.

Figure 2:
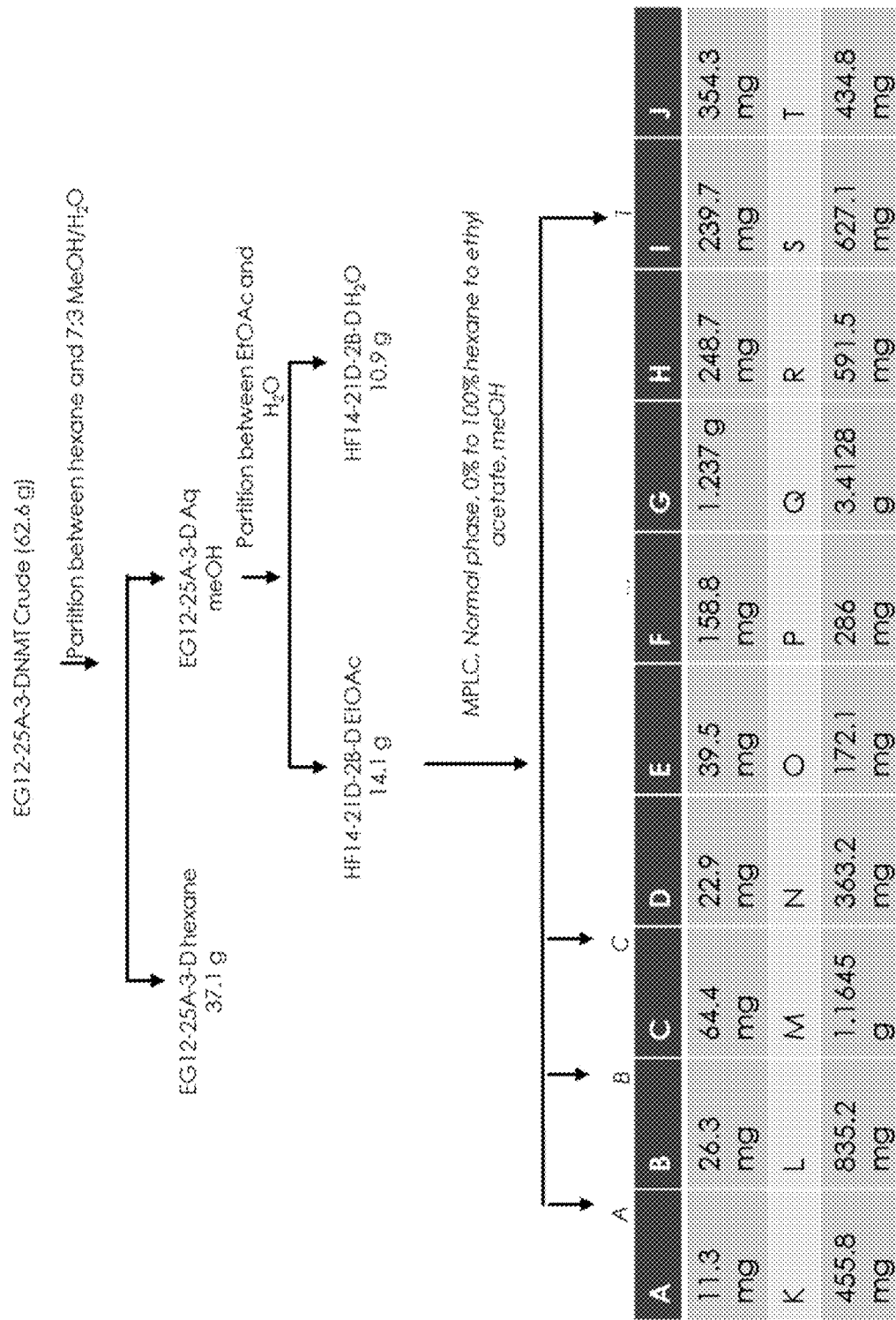
FIG. 2 shows the separation scheme for EG12-25A-3-DNMT as further described in the examples.
Figure 3:
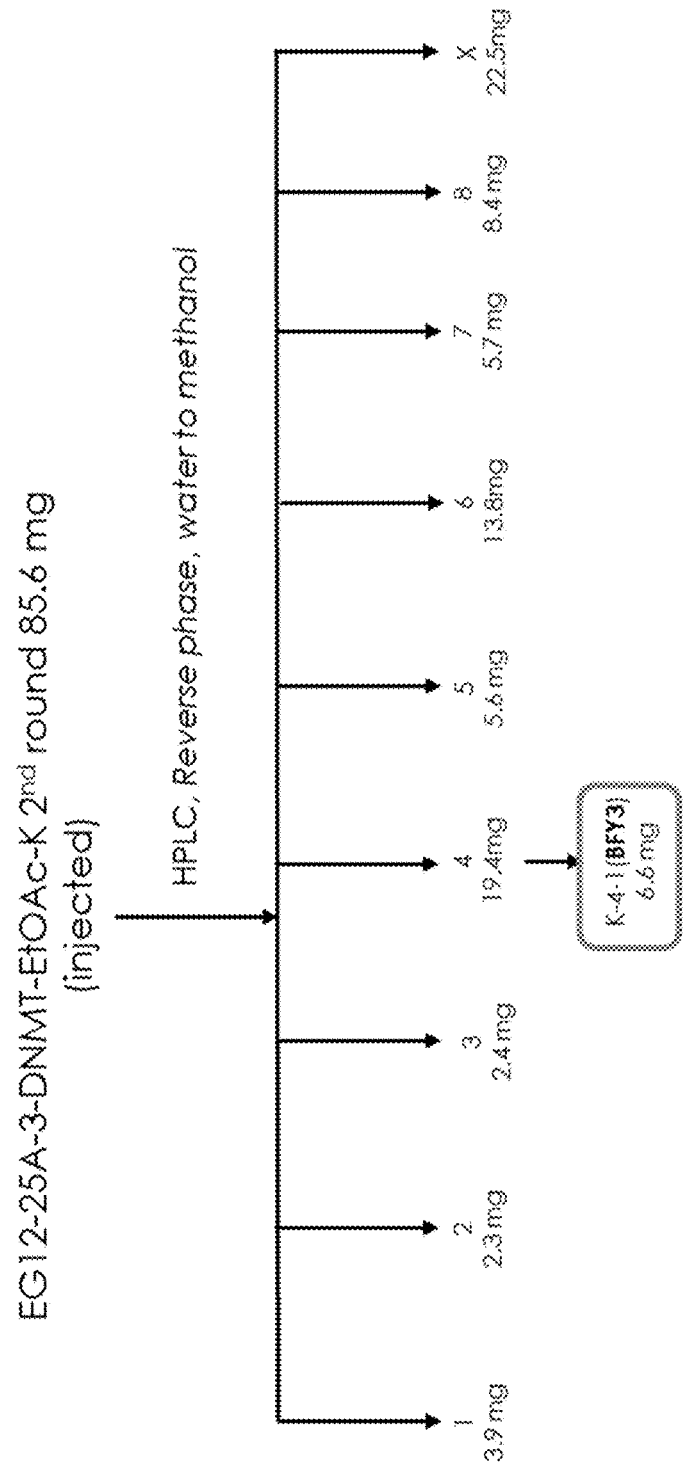
FIG. 3 shows the isolation scheme for BFY3 as further described in the examples.
Figure 4:
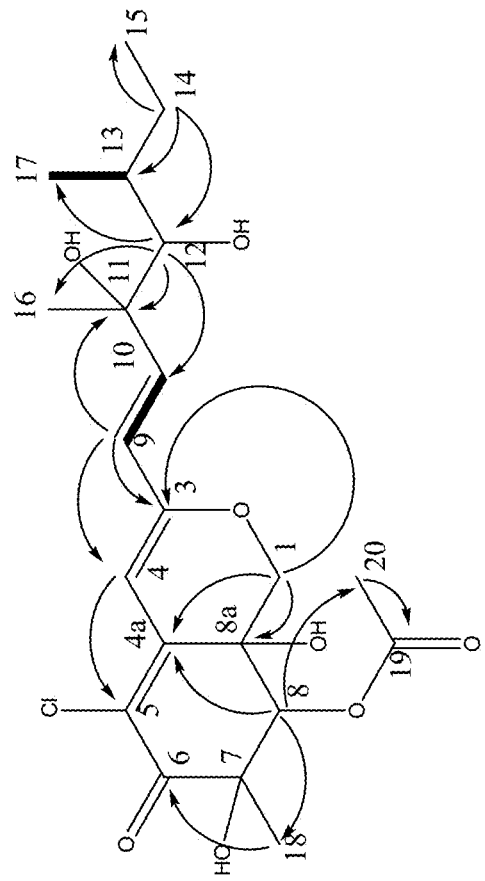
FIG. 4 shows the key COSY (bolded lines) and HMBC (black arrows) of BFY-3.

Fungal strain EG12-25A-3 was inoculated in a larger scale of rice media with 5-azacytidine (DNMT inhibitor) broth (labeled as EG12-25A-3-DNMT) and was cultivated for 21 days. At the same time, the fungal strain sample was sent for identification, and the Shaw lab confirmed this strain is *Penicillium sclerotiorum* by processing the raw FASTA nucleotide sequence and BLASTn. Cultivation was followed by one period of 24-hour extraction in methanol (MeOH) to ethyl acetate (EtOAc) 1:3, and two periods of 24-hour extraction in EtOAc. The crude extract was partitioned between hexanes and 70% aqueous MeOH first, followed by the 70% aqueous methanol layer partitioned between EtOAc and water. The EtOAc layer was dried and treated with silica, with ratio of mass 1:3. Medium pressure liquid chromatography (HPLC) was carried out to fractionate the EtOAc layer, yielding 20 fractions (FIG. 2). The MPLC fractions of the EtOAc layer, along with the hexane layer and the water layer from the previous partition process, were tested against replicating stage *M. tuberculosis* (Mtb), the murine macrophage cell line J774 and *M. abscessus* (Mab). The bioactivity data taken with proton nuclear magnetic resonance ($^1$H NMR) data was used to guide further separation. Table 1. shows the bioassay results. The fractions in the blue rows were considered moderately active against replicating Mtb and Mab, with define cytotoxicity results. The green rows show the fractions with better replicating Mtb bioactivity compared to the blue ones. Active fractions with define peaks in $^1$H NMR were selected and further separated with high performance liquid chromatography (HPLC). After several rounds of separation with normal phase (NP) HPLC and reverse phase (RP) HPLC, two new compounds (BFY-3 and BFY-4), along with nine known compounds, were isolated from the EG12-25A-3-DNMT extract (FIG. 3 and FIG. 4).

TABLE 1

Bioassay data from hexane, water and EtOAc layers, and MPLC fractions from EG12-25A-3-DNMT extract. (data from Dr. Kyle Rohde)

| Compound | MIC (Mtb-rep) (µg/ml) | IC$_{50}$ (J774) (µg/ml) | *M. abscessus* (% inhibition) | | | |
|---|---|---|---|---|---|---|
| | | | 300 µg/ml | 150 µg/ml | 75 µg/ml | 37.5 µg/ml |
| EtOAc-A | n/d | n/d | 0.0 | 0.0 | 0.0 | 0.0 |
| EtOAc-B | ~75 | ~200 | 49.5 | 40.6 | 30.5 | 0.0 |
| EtOAc-C | ~20 | ~100 | 78.1 | 79.6 | 70.7 | 35.3 |
| EtOAc-D | ~10 | ~100 | 62.6 | 67.2 | 50.4 | 0.0 |
| EtOAc-E | ~25 | ~100 | 67.7 | 65.6 | 56.9 | 23.3 |
| EtOAc-F | ~20 | ~50 | 87.3 | 82.3 | 70.3 | 52.8 |
| EtOAc-G | ~15 | ~50 | 92.6 | 88.0 | 65.6 | 58.2 |
| EtOAc-H | 12.43 | ~25 | 92.9 | 89.6 | 70.7 | 34.4 |
| EtOAc-I | ~40 | n/d | 89.7 | 71.1 | 40.9 | 4.4 |
| EtOAc-J | ~50 | n/d | 79.7 | 79.7 | 61.7 | 42.6 |
| EtOAc-K | ~100 | n/d | 42.9 | 31.2 | 9.9 | 0.0 |
| EtOAc-L | ~100 | ~250 | 46.9 | 46.7 | 28.7 | 0.0 |
| EtOAc-M | ~150 | n/d | 96.1 | 83.1 | 62.8 | 51.3 |
| EtOAc-M | ~300 | ~300 | 34.6 | 35.3 | 22.1 | 6.0 |
| EtOAc-O | ~50 | ~50 | 101.9 | 74.4 | 51.9 | 43.8 |
| EtOAc-P | ~150 | ~1 | 54.3 | 47.6 | 14.2 | 6.4 |
| EtOAc-Q | ~200 | n/d | 82.6 | 79.4 | 64.0 | 28.5 |
| EtOAc-R | ~150 | n/d | 78.2 | 77.9 | 62.5 | 15.4 |
| EtOAc-S | ~100 | n/d | 85.6 | 74.6 | 70.4 | 16.6 |
| EtOAc-T | ~100 | n/d | 76.5 | 77.3 | 60.6 | 7.0 |
| Hexane | ~300 | ~200 | 33.9 | 40.9 | 32.6 | 0.0 |
| H$_2$O | n/d | ~300 | 18.5 | 9.2 | 0.0 | 0.0 |

BFY-3 (fraction K-4-1) was isolated as a bright yellow oil, and was found to have the molecular formula of $C_{21}H_{29}ClO_8$, based on HRESIMS (m/z 445.1514 [M+H]$^+$, calculated 445.1585). The intensity ratio of peak m/z 445.1514 and peak m/z 447.1642 is 3:1 indicating the presence of one chlorine atom. Structure elucidation was completed with 1D and 2D NMR spectroscopy, including $^1$H, $^{13}$C, gCOSY, gHSQC and gHMBC spectra. 1D NMR data of BFY3 is shown in Table 2. The $^1$H NMR spectrum combined with the gHSQC spectrum suggested the presence of five methyls ($\delta_H$ 2.04, 1.62, 1.33, 0.89, and 0.85), two methylenes with diastereotopic protons ($\delta_H$ 4.25, 3.98, 1.42 and 1.29), three olefinic protons ($\delta_H$ 6.78, 6.30 and 6.07), and three methines ($\delta_H$ 5.30, 3.44 and 1.72). The $^{13}$C NMR spectrum and the gHSQC spectrum indicated the presence of two carbonyl groups ($\delta_C$ 193.8 and 172.3), six olefinic carbons ($\delta_C$ 162.3, 146.0, 145.6, 122.5, 120.4 and 101.7), and six oxygenated carbons ($\delta_C$ 81.1, 79.2, 77.0, 73.8, 68.4, 68.3). Four exchangeable protons were revealed by the $^1$H NMR spectrum in DMSO-$d_6$.

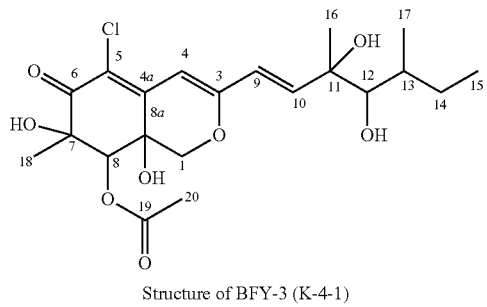

Structure of BFY-3 (K-4-1)

TABLE 2

NMR data of BFY-3 in CD$_3$OD.[a]

| Positions | C, type | H (J in Hz) | HMBC |
|---|---|---|---|
| 1α | 73.8, CH$_2$ | 4.25, d (11.7) | 3, 4a, 7, 8a |
| 1β | | 3.98, d (11.7) | 3, 4a, 7 |
| 3 | 162.3, C | | |
| 4 | 101.7, CH | 6.07, s | 3, 5, 7, 8a |
| 4a | 146.0, C | | |
| 5 | 120.4, C | | |
| 6 | 193.8, C | | |
| 7 | 68.2, C | | |
| 8 | 79.2, CH | 5.30, s | 1, 4a, 6, 18, 19 |
| 8a | 68.4, C | | |
| 9 | 122.5, CH | 6.30, d (15.7) | 3, 4, 4a, 11 |
| 10 | 145.6, CH | 6.78, d (15.7) | 3, 9, 11, 16 |
| 11 | 77.0, C | | |
| 12 | 81.1, CH | 3.44, br s | 10, 11, 16, 17 |
| 13 | 36.4, CH | 1.72, m | 15 |
| 14α | 30.1, CH$_2$ | 1.42, m | 12, 13, 15 |
| 14β | | 1.29, m | 12, 13, 15 |
| 15 | 12.4, CH$_3$ | 0.89, t (7.4) | 13, 14 |
| 16 | 26.5, CH$_3$ | 1.33, s | 10, 11, 12 |
| 17 | 14.8, CH$_3$ | 0.85, d (6.7) | 12, 13, 14 |
| 18 | 27.1, CH$_3$ | 1.62, s | 6, 8 |
| 19 | 172.3, C | | |
| 20 | 20.9, CH$_3$ | 2.04, s | 19 |
| 7-OH | | | |
| 8a-OH | | | |
| 11-OH | | | |
| 12-OH | | | |

[a]$^1$H NMR data recorded at 500 MHz, reported in ppm (multiplicity, J in Hz, integration); $^{13}$C NMR data recorded at 125 MHz; HMBC performed as gHMBCAD and recorded as positions of carbons.

Figure 6:
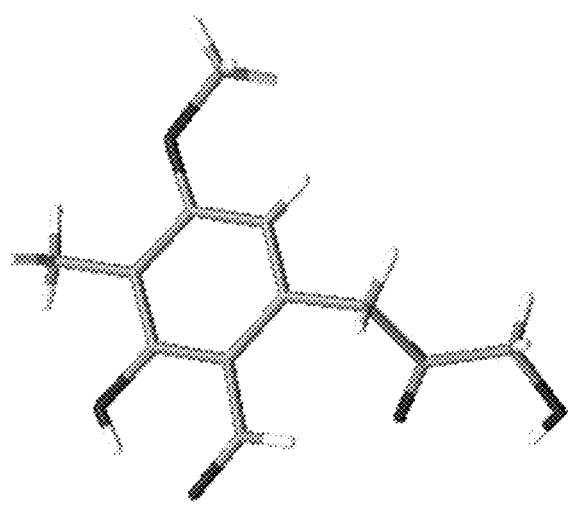
FIG. 6 shows the x-ray crystallography structure of BFY-4.
Figure 7:
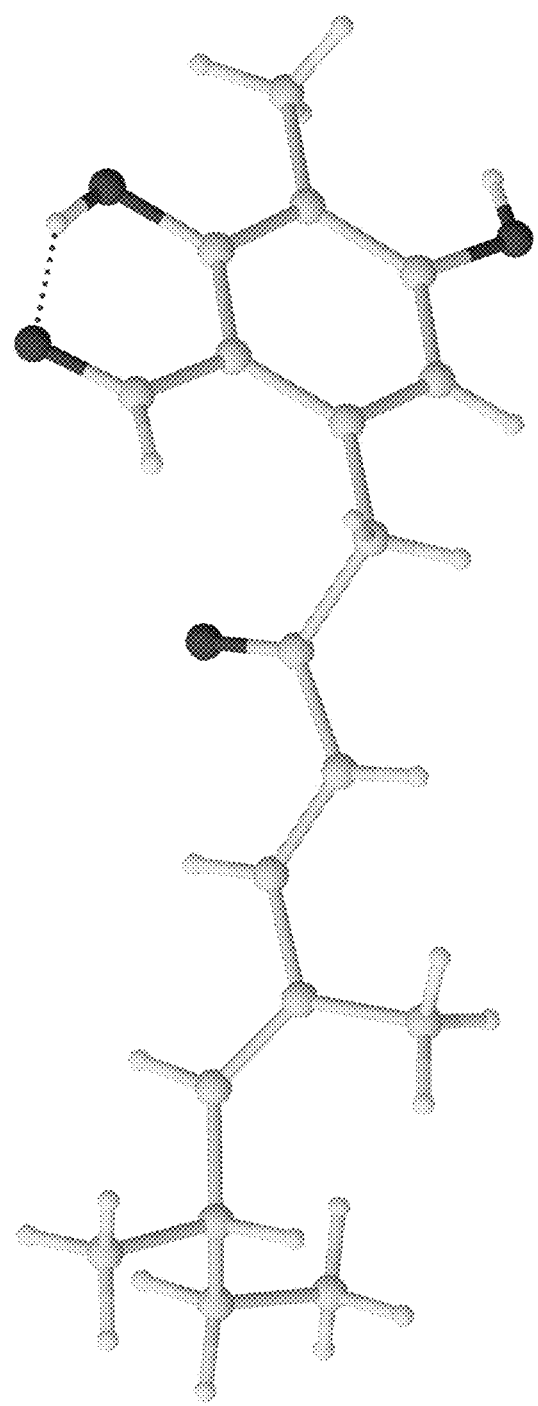
FIG. 7 shows the x-ray crystallography structure of Fraction D.
Figure 8:
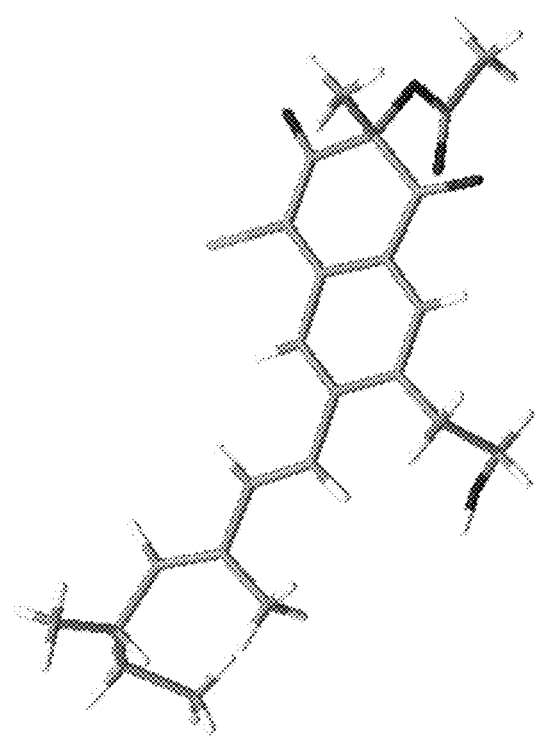
FIG. 8 shows the x-ray crystallography structure of Fraction O-7.
Figure 9:
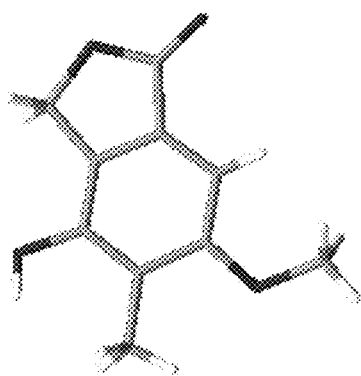
FIG. 9 shows the x-ray crystallography structure of Fraction F-8-3.
Figure 10:
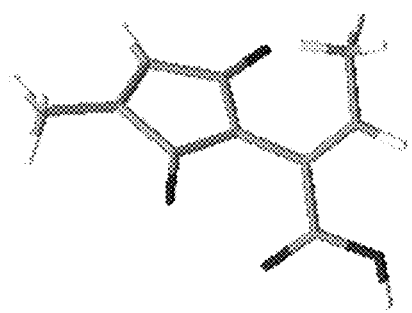
FIG. 10 shows the x-ray crystallography structure of Fraction G-4.

Based on the degree of unsaturation, BFY-3 was determined to be a bicyclic compound with 2 carbonyl groups and six olefinic carbons. $^1$H-$^1$H COSY correlations (H-13/H$_3$-17; H-10/H-9) combined with 2D gHMBC correlations (H$_3$-15/ C-13 and C-14; H$_2$-14/C-12, C-13 and C-15; H$_3$-17/C-12, C-13 and C-14; and H-12/C-10, C-11 and C-17) indicated a chain with C-11, C-12, C-13, C-14 and C-15 (FIG. 4), while C-17 was found to connect with C-13. One of the two open valances on C-11 was assigned to the methyl group C-16, based on gHMBC correlation H-12/C-16. Further connection was built based on gHMBC correlations H-10/C-3, C-9, C-11 and C-16; H-9/C-3, C-4a, C-4, and C-11; H-4/C-3, C-5 and C-8a, which suggested a conjugated system with three olefins, containing C-10, C-9, C-3, C-4, C-4a and C-5. C-10 was found attached to C-11 based on gHMBC correlation H-10/C-16. $^1$H-$^1$H COSY correlation between H-9 and H-10 supported the position of C-9 and C-10. Continuing with analysis of the gHMBC spectrum, H$_2$-1 has correlations to C-3, C-4a and quaternary carbon C-8a. Considering the chemical shift of C-1 ($\delta$ c 73.6) indicating an oxygenated carbon, a six-member ring was built with C-1, C-3, C-4, C-4a, C-8a and an oxygen. gHMBC correlation of H-8/C-1, C-4a and C-6 indicated the methine group C-8 is attached to the six-member ring. Further connection was built based on gHMBC correlations H-8/C-18, C-6; H$_3$-18/C-6, C-8. Based on the previously built six-member-ring, a bicyclic skeleton was revealed, with C-8, C-6, C-7 (attached to Me-18) and C-5 as one of the bridges. An acetate group was found attached to C-8 based on gHMBC correlation between H-8/C-20. Me-20 was assigned based on its correlation with C-19. The chemical shifts of C-11 ($\delta$ c 77.0), C-12 ($\delta$ c 81.1), C-7 ($\delta$ c 68.2) and C-8a ($\delta$ c 68.4), combined with the information of four exchangeable protons, suggested a diol system on position C-11 and C-12, and one hydroxy group each on C-7 and C-8a. The chlorine atom was assigned to the open valence of C-5. Compared to the most related known azaphilone compounds eupenicilazaphilone C and hypocrellone A (FIG. 6) BFY-3 has a unique alcohol group on position C-8a.

Figure 5:
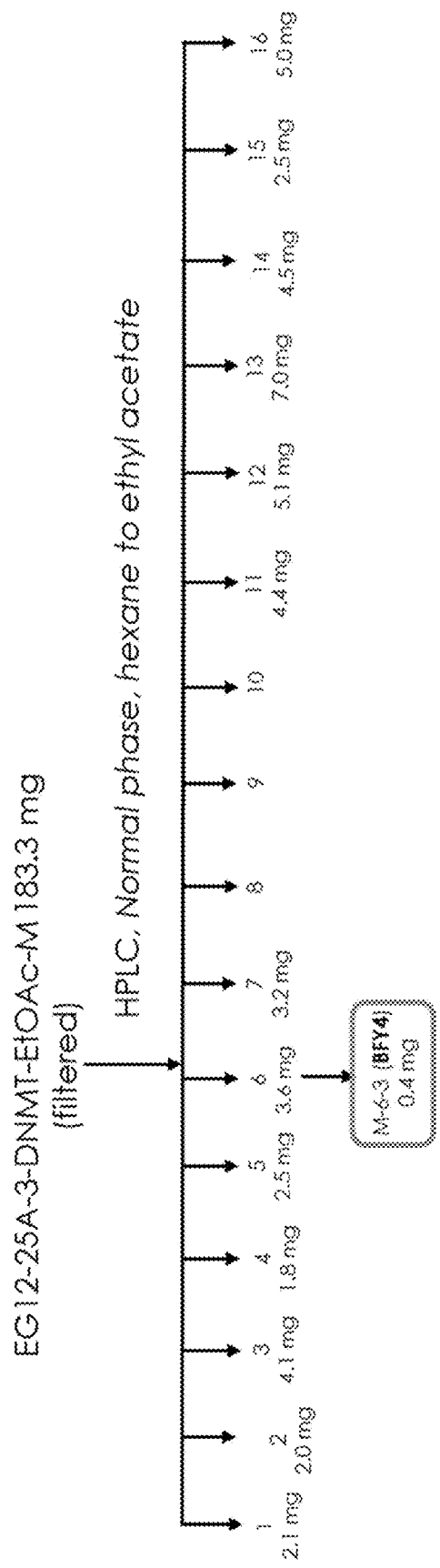
FIG. 5 shows the isolating scheme for BFY4 as further described in the examples.

The other new compound BFY4 was isolated as fraction M-6-3 (FIG. 5). The structure was established and confirmed by X-ray crystallography. 1D $^1$H NMR data is shown in Table 3.

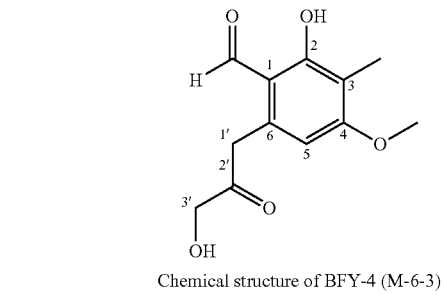 [SMILES: COc1cc(CC(=O)CO)c(C=O)c(O)c1C]

Chemical structure of BFY-4 (M-6-3)

TABLE 3

1D NMR data of M-6-3 in MeOD.[a]

| Position | M-6-3<br>H (J in Hz) |
|---|---|
| 1-CHO | 9.91, s |
| 2 | |
| 3-CH$_3$ | 2.03, s |
| 4-OCH$_3$ | 3.91, s |
| 5 | 6.50, s |
| 6 | |
| 1' | 4.15, s |
| 2' | |
| 3' | 4.36, s |
| 3'-OH | 4.58, br s |

[a]$^1$H NMR data recorded at 500 MHz, reported in ppm (multiplicity, J in Hz, integration)

Several known compounds with the same bicyclic azaphilone skeleton were isolated from the same extract. J-3, K-5-1, and I-7-4 were analyzed based on comparing 1D NMR data with the literature, along with analyzing HESIMS data. These three compounds were identified as possible isomers, based on the same molecular mass. Their NMR data matched with two known compounds eupenicilazaphilone C and hypocrellone A,[18] based on coupling constants related of the chiral centers. The major difference between J-3 and K-5-1 focused on the coupling constant between H-8 and H-8a. The coupling constant value 9.9 Hz in J-3 indicated the position between H-8 and H-8a is anti, while in K-d-d the coupling constant value is 2.9 Hz, suggesting the gauche position. The difference between J-3 and I-7-4 is the coupling constant between H-12 and H-13. The small value of coupling constant in J-3 resulted in the broad singlet of H-12 peak in 1D $^1$H NMR, while in I-7-4 H-12 peak showed as a doublet peak. Comparison of NMR data with the known compounds are shown in Table 4. below. J-3, K-5-1 and I-7-4 are expected to be three different diastereomers (Table 5.).

TABLE 4

1D NMR data comparison of eupenicilazaphilone C, hypocrellone A and J-3 in DMSO-$d_6$.[a]

| position | Eupenicilazaphilone C DMSO C, type | Eupenicilazaphilone C DMSO H (J in Hz) | Hypocrellone A DMSO C, type | Hypocrellone A DMSO H (J in Hz) | J-3 DMSO H (J in Hz) |
|---|---|---|---|---|---|
| 1 | 67.3, $CH_2$ | 3.79, dd (13.6, 10.8) | 67.2, $CH_2$ | 3.79, dd (13.7, 10.9) | 3.78, dd (13.5, 10.9) |
|   |   | 4.49, dd (10.8, 5.0) |   | 4.48, dd (10.8, 5.0) | 4.48, dd (10.7, 4.9) |
| 2 |   |   |   |   |   |
| 3 | 161.7, C |   | 162.0, C |   |   |
| 4 | 100.5, CH | 6.07, s | 100.1, CH | 6.02, s | 6.02, s |
| 4a | 145.0, C |   | 145.2, C |   |   |
| 5 | 118.3, C |   | 118.1, C |   |   |
| 6 | 187.4, C |   | 187.4, C |   |   |
| 7 | 74.0, C |   | 74.0, C |   |   |
| 8 | 72.9, CH | 4.91, d (9.9) | 72.8, CH | 4.91, d (9.9) | 4.91, d (9.9) |
| 8a | 35.4, CH | 3.27, m | 35.5, CH | 3.27, m | 3.27, m |
| 9 | 120.7, CH | 6.29, d (15.7) | 120.2, CH | 6.25, d (15.7) | 6.25, d (15.7) |
| 10 | 144.8, CH | 6.60, d (15.7) | 144.9, CH | 6.70, d (15.7) | 6.70, d (15.7) |
| 11 | 75.3, C |   | 75.0, C |   |   |
| 12 | 77.5, CH | 3.25, m | 79.3, CH | 3.24, m | 3.24, m |
| 13 | 35.7, CH | 1.50, m | 34.4, CH | 1.64, m | 1.64, m |
| 14 | 28.6, $CH_2$ | 1.16, m | 28.6, $CH_2$ | 1.17, m | 1.17, m |
|   |   | 1.33, m |   | 1.31, m | 1.31, m |
| 15 | 11.8, $CH_3$ | 0.81, m | 11.9, $CH_3$ | 0.82, t (7.4) | 0.82, t (7.4) |
| 16 | 25.0, $CH_3$ | 1.20, s | 27.2, $CH_3$ | 1.23, s | 1.23, s |
| 17 | 14.2, $CH_3$ | 0.81, m | 14.0, $CH_3$ | 0.70, d (6.8) | 0.70, d (6.7) |
| 18 | 19.6, $CH_3$ | 1.19, s | 19.5, $CH_3$ | 1.18, s | 1.18, s |
| 19 | 170.2, C |   | 170.2, C |   |   |
| 20 | 20.5, $CH_3$ | 2.15, s | 20.5, $CH_3$ | 2.15, s | 2.15, s |
| 7-OH |   | 5.96, s |   | 5.95, s | 5.94, s |
| 8-OH |   |   |   |   |   |
| 11-OH |   | 4.60, s |   | 4.74, s | 4.74, s |
| 12-OH |   | 4.44, d (6.6) |   | 4.67, d (6.1) | 4.67, d (6.1) |

[a] $^1$H NMR data recorded at 500 MHz, reported in ppm (multiplicity, J in Hz, integration); $^{13}$C NMR data recorded at 125 MHz.

TABLE 5

$^1$H NMR data of I-7-4 and K-5-1 in $CD_3OD$.[a]

| position | I-7-4 MeOD H (J in Hz) | K-5-1 MeOD H (J in Hz) |
|---|---|---|
| 1 | 3.82, dd (10.9, 2.8) | 3.79, dd (10.7, 2.3) |
|   | 4.46, dd (5.0, 5.8) | 4.53, dd (4.8, 5.9) |
| 3 |   |   |
| 4 | 6.13, s | 6.10, s |
| 4a |   |   |
| 5 |   |   |
| 6 |   |   |
| 7 |   |   |
| 8 | 4.98, d (10.0) | 5.47, d (2.9) |
| 8a | 3.38, m | 3.43, m |
| 9 | 6.28, d (15.7) | 6.27, d (15.7) |
| 10 | 6.76, d (15.7) | 6.76, d (15.7) |
| 11 |   |   |
| 12 | 3.41, d (2.1) | 3.42, d (2.2) |
| 13 | 1.71, m | 1.71, m |
| 14 | 1.41, m | 1.41, m |
|   | 1.28, m | 1.28, m |
| 15 | 0.91, t (7.4) | 0.90, t (7.4) |
| 16 | 1.31, s | 1.42, s |
| 17 | 0.85, d (6.8) | 0.85, d (6.8) |
| 18 | 1.25, s | 1.31, s |
| 19 |   |   |
| 20 | 2.19, s | 2.02, s |
| 7-OH |   |   |
| 8-OH |   |   |
| 11-OH |   |   |
| 12-OH |   |   |

[a] $^1$H NMR data recorded at 500 MHz, reported in ppm (multiplicity, J in Hz, integration).

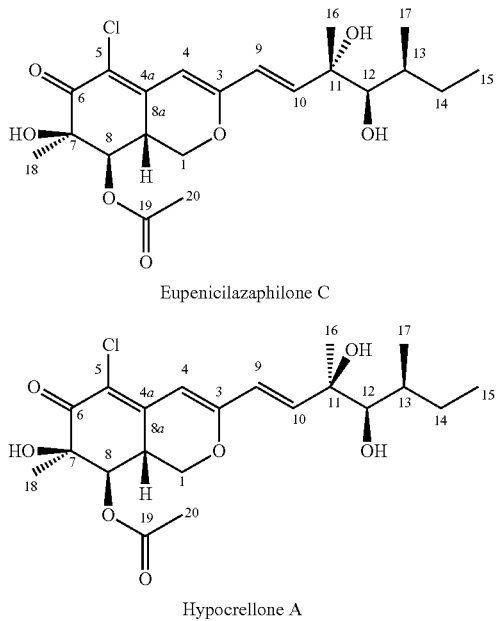

Eupenicilazaphilone C

Hypocrellone A

TABLE 6

1D NMR data of M-8-9-6 and L-8-4-8 in and MeOD and DMSO-$d_6$, compared with known compounds geumsanol C and geusanol D.[a]

| position | M-8-9-6 MeOD C, type | H (J in Hz) | M-8-9-6 DMSO C, type | H (J in Hz) |
|---|---|---|---|---|
| 1 | 70.1, $CH_2$ | 3.76, dd (10.9, 2.7) 4.76, dd (5.4, 5.2) | 68.7, $CH_2$ | 4.58, dd (10.7, 5.4) 3.68, dd (13.5, 11.0) |
| 3 | 162.3, C | | 159.7, C | |
| 4 | 105.0, CH | 5.74, s | 103.7, CH | 5.70, s |
| 4a | 154.7, C | | 151.5, C | |
| 5 | 116.9, CH | 5.69, d (1.2) | 116.2, CH | 5.56, d (1.3) |
| 6 | 199.4, C | | 197.0, C | |
| 7 | 75.9, C | | 74.5, C | |
| 8 | 75.7, CH | 3.40, ovl | 74.0, CH | 3.20, ovl |
| 8a | 37.4, CH | 3.05, m | 36.0, CH | 2.84, m |
| 9 | 122.7, CH | 6.18, d (15.7) | 120.5, CH | 6.05, d (15.7) |
| 10 | 143.7, CH | 6.66, d (15.7) | 142.9, CH | 6.53, d (15.7) |
| 11 | 76.69, C | | 75.0, C | |
| 12 | 81.00, CH | 3.42, ovl | 79.4, CH | 3.20, ovl |
| 13 | 36.4, CH | 1.69, m | 34.6, CH | 1.59, m |
| 14 | 30.1, $CH_2$ | 1.42, m 1.28, m | 28.7, $CH_2$ | 1.26, m 1.13, m |
| 15 | 12.2, $CH_3$ | 0.90, t (7.4) | 12.0, $CH_3$ | 0.76, t (7.4) |
| 16 | 26.4, $CH_3$ | 1.31, s | 27.4, $CH_3$ | 1.16, s |
| 17 | 14.3, $CH_3$ | 0.86, d (6.8) | 14.2, $CH_3$ | 0.66, d (6.8) |
| 18 | 19.6, $CH_3$ | 1.37, s | 19.5, $CH_3$ | 1.16, s |
| 19 | | | | |
| 20 | | | | |
| 7-OH | | | | 5.17, s |
| 8-OH | | | | 5.14, d (7.9) |
| 11-OH | | | | 4.68, s |
| 12-OH | | | | 4.62, d (6.1) |

| position | L-8-4-8 MeOD C, type | H (J in Hz) | L-8-4-8 DMSO C, type | H (J in Hz) |
|---|---|---|---|---|
| 1 | 69.3, $CH_2$ | 3.75, dd (10.8, 2.8) 4.43, dd (5.2, 5.5) | 67.7, $CH_2$ | 4.39, dd (10.7, 5.1) 3.65, dd (13.5, 11.1) |
| 3 | 162.3, C | | 160.1, C | |
| 4 | 105.0, CH | 5.79, s | 103.8, CH | 5.80, s |
| 4a | 153.9, C | | 151.0, C | |
| 5 | 117.1, CH | 5.76, d (1.6) | 116.3, CH | 5.69, br s |
| 6 | 197.2, C | | 195.2, C | |
| 7 | 75.3, C | | 73.6, C | |
| 8 | 76.2, CH | 4.93, d (10.7) | 74.7, CH | 4.76, d (10.0) |
| 8a | 36.5, CH | 1.70, m | 34.8, CH | 3.10, m |
| 9 | 122.6, CH | 6.19, d (15.7) | 120.6, CH | 6.08, d (15.7) |
| 10 | 144.2, CH | 6.66, d (15.7) | 143.6, CH | 6.55, d (15.7) |
| 11 | 76.9, C | | 75.3, C | |
| 12 | 81.1, CH | 3.41, d (1.7) | 79.7, CH | 3.24, br d (4.4) |
| 13 | 36.5, CH | | 34.8, CH | 1.60, m |
| 14 | 30.2, $CH_2$ | 1.41, m 1.28, m | 28.9, $CH_2$ | 1.28, m 1.16, m |
| 15 | 12.4, $CH_3$ | 0.90, t (7.4) | 12.2, $CH_3$ | 0.79, t (7.4) |
| 16 | 26.5, $CH_3$ | 1.31, s | 27.5, $CH_3$ | 1.19, s |
| 17 | 14.5, $CH_3$ | 0.85, d (6.8) | 14.4, $CH_3$ | 0.68, d (6.7) |
| 18 | 19.7, $CH_3$ | 1.25, s | 19.4, $CH_3$ | 1.09, s |
| 19 | 172.6, C | | 171.0, C | |
| 20 | 20.8, $CH_3$ | 2.20, s | 20.7, $CH_3$ | 2.12, s |
| 7-OH | | | | 5.75, s |
| 8-OH | | | | |
| 11-OH | | | | 4.80, s |
| 12-OH | | | | 4.72, d (5.8) |

| position | Geumsanol C DMSO C, type | H (J, in Hz) | Geumsanol D DMSO C, type | H (J, in Hz) |
|---|---|---|---|---|
| 1 | 68.5, $CH_2$ | 4.62, ovl 3.73, dd (13.5, 10.8) | 67.3, $CH_2$ | 4.42, dd (10.7, 5.2) 3.67, dd (13.5, 10.8) |
| 3 | 159.5, C | | 159.8, C | |
| 4 | 103.5, CH | 5.74, s | 104.4, CH | 5.81, s |
| 4a | 151.1, C | | 150.2, C | |
| 5 | 116.0, CH | 5.59, d (1.2) | 115.9, CH | 5.68, d (1.7) |
| 6 | 196.7, C | | 194.5, C | |
| 7 | 74.3, C | | 73.2, C | |
| 8 | 73.9, CH | 3.24, ovl | 74.3, CH | 4.77, d (9.9) |
| 8a | 35.9, CH | 2.89, m | 34.4, CH | 3.12, m |
| 9 | 120.3, CH | 6.09, d (15.7) | 120.1, CH | 6.11, d (15.7) |
| 10 | 142.7, CH | 6.57, d (15.7) | 143.2, CH | 6.57, d (15.7) |
| 11 | 74.8, C | | 74.8, C | |
| 12 | 79.2, CH | 3.24, ovl | 79.2, CH | 3.24, dd (5.9, 1.5) |
| 13 | 34.4, CH | 1.63, m | 34.4, CH | 1.61, m |
| 14 | 28.5, $CH_2$ | 1.31, m 1.18, m | 28.6, $CH_2$ | 1.31, m 1.18, m |
| 15 | 11.8, $CH_3$ | 0.82, t (7.4) | 11.9, $CH_3$ | 0.81, t (7.4) |
| 16 | 27.3, $CH_3$ | 1.21, s | 27.2, $CH_3$ | 1.21, s |
| 17 | 14.9, $CH_3$ | 0.71, d (6.8) | 14.0, $CH_3$ | 0.70, d (6.8) |
| 18 | 19.3, $CH_3$ | 1.20, s | 19.0, $CH_3$ | 1.10, s |
| 19 | | | 170.3, C | |
| 20 | | | 20.5, $CH_3$ | 2.14, s |
| 7-OH | | 5.18, s | | 5.62, s |
| 8-OH | | 5.10, d (8.3) | | |
| 11-OH | | 4.66, s | | 4.68, s |
| 12-OH | | 4.62, ovl | | 4.62, d (6.0) |

[a] $^1$H NMR recorded at 500 MHz, reported in ppm (multiplicity, J in Hz, integration); $^{13}$C recorded at 125 MHz.

M-8-9-6 was identified to have same structure of the known compound geumsanol C or its isomer because the 1D proton and carbon NMR data matched with guemsanol C, along with the matching molecular mass.[19] Compared to the $^1$H NMR spectrum of M-8-9-6, L-8-4-8 has an acetyl methyl group with a $\delta_H$ 2.20 in $CD_3OD$. Further comparison of the NMR spectrum indicated L-8-4-8 matched with that of geumsanol D (2.26), including chemical shifts and coupling constants. L-8-4-8 was identified as geumsanol D or its isomer.[19] The 1D NMR data is shown in Table 5.

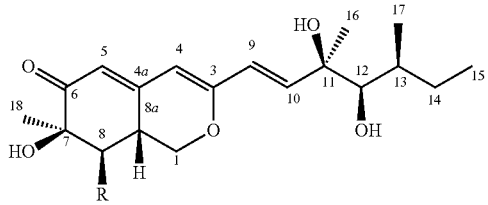

R = OH, geumsanol C
R = OAC, geumsanol D
Structures of the geumsanols

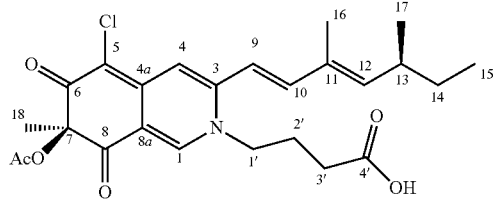

Structure of isochromophilone IX

Fraction M-8-13-5 was isolated as a dark red solid. After comparing 1D NMR data with the literature, M-8-13-5 matched with a known compound isochromophilone IX, which indicated the compound M-8-13-5 is same or an isomer of isochromophilone IX. Isochromophione IX was first isolated in 2003 and showed inhibition against MRSA with MIC of 50 μg/mL.[20] Comparison of 1D NMR data between M-8-13-5 and isochromophilone IX is shown in Table 7.

TABLE 7

1D NMR data of M-8-13-5 and isochromophilone IX in CDCl$_3$.[a]

| | M-8-13-5 CDCl$_3$ | | Isochromophilone IX CDCl$_3$ | |
|---|---|---|---|---|
| Position | C, type | H (J in Hz) | C, type | H (J in Hz) |
| 1 | 141.4, CH | 7.83, s | 141.2, CH | 7.80, s |
| 3 | 144.9, C | | 148.1, C | |
| 4 | 111.5, CH | 7.05, s | 111.5, CH | 7.05, s |
| 4a | 148.1, C | | 144.7, C | |
| 5 | 102.0, C | | 102.1, C | |
| 6 | 184.3, C | | 184.4, C | |
| 7 | 84.8, C | | 84.7, C | |
| 8 | 193.8, C | | 193.8, C | |
| 8a | 114.8, C | | 114.9, C | |
| 9 | 114.4, CH | 6.30, d (15.3) | 114.3, CH | 6.28, d (15.0) |
| 10 | 145.4, CH | 6.99, d (15.3) | 145.5, CH | 6.99, d (15.0) |
| 11 | 132.0, C | | 132.0, C | |
| 12 | 148.3, CH | 5.72, d (9.7) | 148.4, CH | 5.71, brd (9.5) |
| 13 | 35.0, CH | 2.49, m | 35.0, CH | 2.47, m |
| 14 | 30.0, CH$_2$ | 1.45, m | 30.0, CH$_2$ | 1.44, ddq (13.0, 6.0, 8.0) |
| | | 1.37, m | | 1.34, ddq (13.0, 6.0, 8.0) |
| 15 | 12.0, CH$_3$ | 0.89, t (7.4) | 12.0, CH$_3$ | 0.88, t (8.0) |
| 16 | 20.2, CH$_3$ | 1.03, d (6.7) | 20.2, CH$_3$ | 1.02, d (6.5) |
| 17 | 12.5, CH$_3$ | 1.88, s | 12.5, CH$_3$ | 1.87, s |
| 18 | 23.2, CH$_3$ | 1.55, s | 23.2, CH$_3$ | 1.55, s |
| 7-OAc | 170.3, C | | 170.2, C | |
| 7-OAc | 20.3, CH$_3$ | 2.16, s | 20.3, CH$_3$ | 2.16, s |
| 1' | 53.4, CH$_2$ | 3.99, t (7.4) | 53.4, CH$_2$ | 3.96, t (7.5) |
| 2' | 25.1, CH$_2$ | 2.07, m | 25.0, CH$_2$ | 2.05, m |
| 3' | 30.2, CH$_2$ | 2.49, t (6.2) | 30.0, CH$_2$ | 2.51, t (6.5) |
| 4' | 175.4, C | | 175.2, C | |

[a] $^1$H NMR recorded at 500 MHz, reported in ppm (multiplicity, J in Hz, integration); $^{13}$C NMR data recorded at 125 MHz.

Several known compounds with identified stereochemistry were also isolated from the same fungal extract. Fraction D, confirmed as 2,4-dihyroxy-6-(5,7-dimethyl-2-oxo-trans-3-trans-5-nonadienyl)-3-methylbenzaldehyde,[21] was the first isolated compound from this fungal extract. It was reported to induce severely impaired heart morphology and curved trunk in exposed zebrafish embryos, with no reported TB bioactivity data. The structure was confirmed by X-ray crystallography.

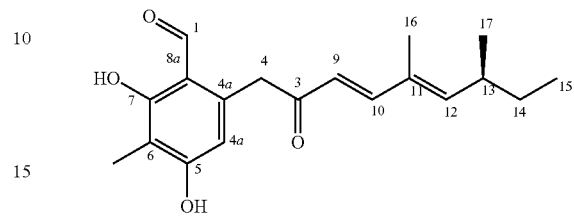

Chemical structure of fraction D

TABLE 8

1D NMR data of D and 2,4-dihyroxy-6-(5,7-dimethyl-2-oxo-trans-3-trans-5-nonadienyl)-3-methylbenzaldehyde in CDCl$_3$.[a]

| position | CDCl3 H (J in Hz) | CDCl3 H (J in Hz) |
|---|---|---|
| 2-OH | 12.63, s | 12.64, s |
| 1-CHO | 9.86, s | 9.85, s |
| 4'-H | 7.35, d (15.7) | 7.34, d (15.7) |
| 4-OH | | 6.55, s |
| 3'-H | 6.19, d (15.7) | 6.18, d (15.7) |
| 5-H | 6.18, s | 6.16, s |
| 6'-H | 5.82, d (9.7) | 5.57, d (9.9) |
| 1'-H | 4.08, s | 4.07, s |
| 7'-H | 2.47, m | 2.48, m |
| 3-CH3 | 2.05, s | 2.05, s |
| 5'-CH3 | 1.80, s | 1.79, s |
| 8'-H | 1.43, m | 1.40, m |
| 7-CH3 | 1.00, d (6.4) | 1.00, d (6.6) |
| 9'-H | 0.86, t (7.1) | 0.85, t (7.2) |

[a] $^1$H NMR data recorded at 400 MHz, reported in ppm (multiplicity, J in Hz, integration)

Fraction O-7 was isolated as a dark red crystal. HRESIMS suggested ink 434.1796 [M+H]$^+$, calculated 434.1734, indicating the molecular formula is $C_{23}H_{28}NO_5Cl$. The $^1$H NMR spectrum of O-7 was compared to the literature and it matched with a known compound isochromophilone VI based on chemical shifts, peak splitting pattern and coupling constants. X-ray crystallography determined that O-7 is Isochromophilone VI, which was first reported in 1995.[22] It was reported to have bioactivity against S. pyogenes and S. typhimurium, while TB activity was not tested. 1D NMR data is shown in Table 2.8 along with data of isochromophilone VI.[20]

TABLE 2.8

1D NMR data of O-7 and isochromophilone VI in CDCl$_3$.[a]

| | O-7 CDCl$_3$ | Isochromophilone VI CDCl$_3$ | |
|---|---|---|---|
| Position | H (J in Hz) | C, type | H (J in Hz) |
| 1 | 7.86, s | 142.3, CH | 7.91, s |
| 3 | | 145.5, C | |
| 4 | 7.04, s | 111.9, CH | 7.05, s |
| 4a | | 149.0, C | |
| 5 | | 101.6, C | |
| 6 | | 184.2, C | |

TABLE 2.8-continued

1D NMR data of O-7 and isochromophilone VI in $CDCl_3$.[a]

| | O-7 $CDCl_3$ | | Isochromophilone VI $CDCl_3$ |
|---|---|---|---|
| Position | H (J in Hz) | C, type | H (J in Hz) |
| 7 | | 84.8, C | |
| 8 | | 193.9, C | |
| 8a | | 114.7, C | |
| 9 | 6.26, d (15.4) | 114.9, CH | 6.27, d (15.3) |
| 10 | 6.95, d (15.2) | 145.5, CH | 6.94, d (15.3) |
| 11 | | 131.7, C | |
| 12 | 5.71, d (9.6) | 148.3, CH | 5.71, brd (9.6) |
| 13 | 2.49, m | 35.0, CH | 2.47, m |
| 14 | 1.44, m | 30.0, $CH_2$ | 1.44, ddq (13.5, 7.2, 7.5) |
| | 1.34, m | | 1.34, ddq (13.5, 5.4, 7.5) |
| 15 | 0.89, t (7.3) | 12.0, $CH_3$ | 0.88, t (7.5) |
| 16 | 1.03, d (6.5) | 20.2, $CH_3$ | 1.02, d (6.0) |
| 17 | 1.86, s | 12.6, $CH_3$ | 1.84, s |
| 18 | 1.57, s | 23.3, $CH_3$ | 1.54, s |
| 7-Oac | | 170.4, C | |
| 7-OAc | 2.17, s | 20.3, $CH_3$ | 2.15, s |
| 1' | 4.04, m | 55.7, $CH_2$ | 4.05, ddd (14.4, 4.8, 4.8) |
| | | | 4.02, ddd (12.9, 4.8, 4.8) |
| 2' | 3.97, m | 60.7, $CH_2$ | 3.92, ddd (12.9, 4.8, 4.8) |
| | | | 3.91, ddd (12.9, 4.8, 4.8) |

[a]$^1$H NMR data recorded at 500 MHz, reported in ppm (multiplicity, J in Hz, integration).

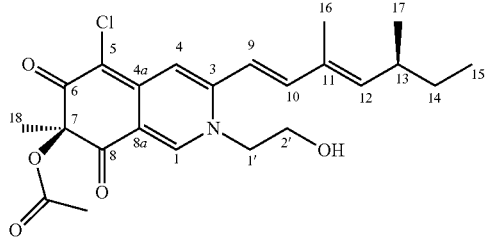

Chemical structure of fraction O-7

Fraction F-8-3 was eluted from reverse phase with methanol and water, and it was crystallized. Further data collected by X-ray crystallography indicated F-8-3 is a known compound 4-hydroxy-6-methoxy-5-methyl-1(3H)-isobenzofuranone.[23] $^1$H NMR data was not able to obtain resulting from limited mass.

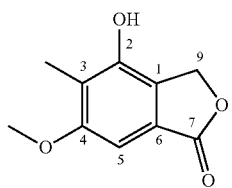

Crystal structure and chemical structure of fraction F-8-3

The major compound from this fungal extract was isolated from fraction G. The fraction G-4 (was recrystallized as snow-flake shape. The structure was identified by X-ray crystallography as pencolide, a well-studied fungal metabolite since 1963.[24] It was reported to show inhibition to *S. pyogenes, S. aureus, S. typhimurium* E. co/i and *C. albicans*.[24] 1D NMR data is shown in Table 9. Comparing to the literature data of pencolide, G-4 matched with pencolide with chemical shift and coupling constants.

TABLE 9

1D NMR data of G-4 in $CDCl_3$,[a] compared with known compound pencolide.[26]

| | G-4 $CDCl_3$ | | Pencolide $CDCl_3$ |
|---|---|---|---|
| Position | H (J in Hz) | C, type | H (J in Hz) |
| 1 | | 167.3, C | |
| 2 | | 123, C | |
| 3 | 7.42, q (7.1) | 145.3, CH | 7.40, q (7.0) |
| 4 | 1.82, d (7.1) | 14.7, $CH_3$ | 1.81, d (7.0) |
| 2' | | 170.2, C | |
| 3' | | 146.7, C | |
| 4' | 6.46, q (1.8) | 128.3, CH | 6.46, q (2.0) |
| 5' | | 169.1, C | |
| 6' | 2.14, d (1.7) | 11.7, $CH_3$ | 2.13, d (2.0) |

[a]$^1$H NMR data recorded at 400 MHz, reported in ppm (multiplicity, J in Hz, integration).

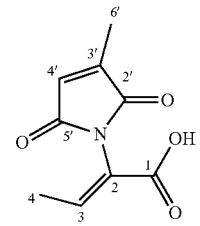

chemical structure of fraction G-4

Bioactivity of Anti-*tuberculosis* Isolates

Compound J-3, O-7, D, F-8-3, M-6-3 and G-4 were tested against replicating Mtb. Cytotoxicity assay was screened with J774 macrophages. F-8-3, M-6-3 and G-4 were also screened against Mab. Results are shown below in Table 10.

TABLE 10

TB bioactivity data of pure compounds isolated from EG12-25A-3-DNMT extract.

| Comsound | MIC (Mtb-rep) (μg/ml) | IC50 (J774) (μg/ml) | *M. abscessus* (μg/ml) |
|---|---|---|---|
| EtOAc-J-3 | ~150 | ~300 | |
| EtOAc-O-7 | 18.6 | ~200 | |
| EtOAc-D | ~50 | ~200 | |
| EtOAc-F-8-3 | 200 | | 200 |
| EtOAc-G-4 | 50 | | 100 |
| EtOAc-M-6-3 | 50 | | 100 |

Figure 11:
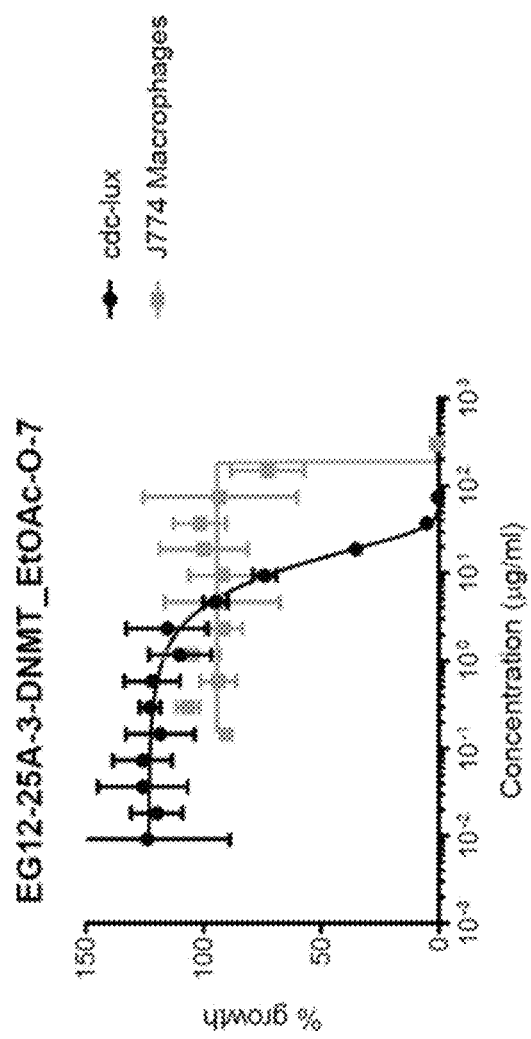
FIG. 11 shows the bioactivity and cytotoxicity of Fraction O-7 obtained as further described in the examples.

Among these tested samples, O-7, determined as the known compound isochromophilone VI, showed MIC=18 μg/ml, $IC_{50}$=200 μg/mL for a selectivity index (SI)=10.78 (FIG. 11). This result could be considered as a starting point for potential hit-to-lead optimization. At the same time, isochromophilone VI is the first naturally occurring nitrogen-containing azaphilone derivative that is reported with antimycobacterial activity.

CONCLUSION

Under epigenetic treatment, 11 compounds were isolated from the EG12-25A-3-DNMT extract. Among these compounds, two compounds, BFY-3 and BFY-4 have new skeletons. The relative stereochemistry on position C-12 and C-13 would be determined by Murata's method. C—H coupling constants will be obtained by HSQMBC spectra. The acetate group attached on C-8 would be hydrolysed to a secondary alcohol. Acetonide formation would be applied on C-7/C-8 and C-11/C-12 to determine the relative stereochemistry. Mosher's method will be applied to the secondary alcohols on C-8 and C-12 to indicate the absolute stereochemistry, and further indicate the absolute stereochemistry of C-7, C-11 and C-13. Five compounds, J-3, I-7-4, K-5-1, M-8-9-6 and L-8-4-8 were identified as known compounds, and the stereochemistry needs to be further determined using the method described above. At the same time, computational calculations would be applied to predict chemical shifts with different diastereomers. Four crystals were isolated, including D, 0-7, F-8-3 and G-4. Six of the pure compounds were tested against replicating Mtb, Mab and J774. O-7 showed promising bioactivity against replicating Mtb, with low cytotoxicity, which makes it promising as a lead compound for further drug development.

REFERENCES

Each of the below publications is hereby incorporated by reference in its entirety for all purposes:
(1) Elkington, P; Tebruegge, M; Mansour S, *tuberculosis*: an infection-initiated autoimmune disease? *Trends. Immunol.*, 2016, 37, 815-818
(2) Kiazyk, S.; Ball, T. Latent *tuberculosis* infection: an overview. *Can. Commun. Dis. Rep.* 2017, 43, 62-66.
(3) Khan, M. K, Islam, M. N, Ferdous, J, Alam, M. M. An overview on epidemiology of *tuberculosis. Mymensingh Med. J.* 2019, 28, 259-266. https://europepmc.org/article/med/30755580 (accessed Jan. 6, 2020).
(4) Churchyard, G. J.; Swindells, S. Controlling Latent TB *tuberculosis* infection in high-burden countries: a neglected strategy to end TB. *PLoS Med.* 2019, 16, e1002787. https://doi.org/10.1371/journal.pmed.1002787.
(5) Lee, M.; Mok, J.; Kim, D. K.; Shim, T. S.; Koh, W.-J.; Jeon, D.; Lee, T.; Lee, S. H.; Kim, J. S.; Park, J. S.; Lee, J. Y.; Kim, S. Y.; Lee, J. H.; Jo, K.-W.; Jhun, B. W.; Kang, Y. AAhn, J. H.; Kim, C.-K.; Shin, S.; Song, T.; Shin, S. J.; Kim, Y. R.; Ahn, H.; Hahn, S.; Won, H. J.; Jang, J. Y.; Cho, S. N.; Yim, J.-J. Delamanid, Linezolid, Levofloxacin, and pyrazinamide for the treatment of patients with fluoroquinolone-sensitive multidrug-resistant *tuberculosis* (treatment shortening of MDR-TB using existing and new drugs, MDR-END): study protocol for a phase II/III, multicenter, randomized, open-label clinical trial *Trials* 2019, 20, 57. https://doi.org/10.1186/s13063-018-3053-1.
(6) Tsang, C. A.; Shah, N.; Armstrong, L. R.; Marks, S. M. Eligibility for a shorter treatment regimen for multidrug-resistant *tuberculosis* in the united states, 2011-2016. *Clin. Infect. Dis.* 2020, 70, 907-916 https://doi.org/10.1093/cid/ciz263.
(7) Asif, M. An overview on fluoroquinolone drugs for the treatment of tubercular infection. *J. Med. Chem.* Sci. 2019, 2, 172-176. https://doi.org/10.26655/jmchemsci.2019.8.7.
(8) Cheng, Z.; Pan, J.-H.; Tang, W.; Chen, Q.; Lin, Y. Biodiversity and biotechnological potential of mangrove-associated fungi. *J. For. Res.* 2009, 20, 63-72. https://doi.org/10.1007/s11676-009-0012-4.
(9) Mangrove Species Profiles https://www.floridamuseum.ufl.edu/southflorida/habitats/mangroves/species/ (accessed Jan. 7, 2020).
(10) Kumaresan, V. Occurrence, Distribution and bioactive potential of mangrove fungal endophytes: an appraisal. *KAVAKA,* 2017, 48, 44-49.
(11) Wen, S.; Fan, W.; Guo, H.; Huang, C.; Yan, Z.; Long, Y. Two new secondary metabolites from the mangrove endophytic fungus *pleosporales* Sp. SK7. *Nat. Prod. Res.* 2019, 0, 1-7. https://doi.org/10.1080/14786419.2019.1598993.
(12) Zhang, L.; Niaz, S. I.; Khan, D.; Wang, Z.; Zhu, Y.; Zhou, H.; Lin, Y.; Li, J.; Liu, L. Induction of diverse bioactive secondary metabolites from the mangrove endophytic fungus *Trichoderma* sp. (strain 307) by co-cultivation with *Acinetobacter johnsonii* (strain B2). *Mar. Drugs.* 2017, 15, 35. https://doi.org/10.3390/md15020035.
(13) Ding, B.; Wang, Z.; Huang, X.; Liu, Y.; Chen, W.; She, Z. Bioactive α-pyrone meroterpenoids from mangrove endophytic fungus *Penicillium* sp. *Nat. Prod. Res.* 2016, 30, 2805-2812. https://doi.org/10.1080/14786419.2016.1164702.
(14) Björn, B. H.; Barbara, B.; Regina, H.; Axel, Z. Big effects from small changes: possible ways to explore nature's chemical diversity. *ChemBioChem.* 2002, 3, 619-627. https://doi.org/10.1002/1439-7633(20020703)3:7<619::AID-CBIC619>3.0.CO; 2-9.
(15) Tresner, H. D.; Hayes, J. A. Sodium chloride tolerance of terrestrial fungi. *Appl. Microbiol.* 1971, 22, 210-213.
(16) Epigenetic modification increases susceptibility to obesity and predicts fatty liver https://medicalxpress.com/news/2016-05-epigenetic-modification-susceptibility-obesity-fatty.html (accessed Jan. 6, 2020).
(17) Demers, D. H.; Knestrick, M. A.; Fleeman, R.; Tawfik, R.; Azhari, A.; Souza, A.; Vesely, B.; Netherton, M.; Gupta, R.; Colon, B. L.; Rice, C. A.; Rodriguez-Perez, M. A.; Rohde, K. H.; Kyle, D. E.; Shaw, L. N.; Baker, B. J. Exploitation of mangrove endophytic fungi for infectious disease drug discovery. *Mar. Drugs.* 2018, 16, 376. https://doi.org/10.3390/md16100376.
(18) Gu, B.-B.; wu, Y.; Tang, J.; Jiao, W.; Li, L.; Sun, F.; Wang, S.-P.; Yang, F.; Lin, H.-W. Azaphilone and isocoumarin derivatives from the sponge-derived fungus *Eupenicillium* sp. 6A-9. *Tetrahedron. Lett.* 2018, 59, 3345-3348. https://doi.org/10.1016/j.tetlet.2018.06.057.
(19) Son, S.; Ko, S.-K.; Kim, J. W.; Lee, J. K.; Jang, M.; Ryoo, I.-J.; Hwang, G. J.; Kwon, M. C.; Shin, K.-S.; Futamura, Y.; Hong, Y.-S.; Oh, H.; Kim, B. Y.; Ueki, M.; Takahashi, S.; Osada, H.; Jang, J.-H.; Ahn, J. S. Structures and biological activities of azaphilones produced by *Penicillium* sp. kcb11a109 from a ginseng field. *Phytochemistry* 2016, 122, 154-164. https://doi.org/10.1016/j.phytochem.2015.12.008.
(20) Michael, A. P.; Grace, E. J.; Kotiw, M.; Barrow, R. A. Isochromophilone IX, a novel gaba-containing metabolite isolated from a cultured fungus, *Penicillium* sp. *Aust. J. Chem.* 2003, 56, 13. https://doi.org/10.1071/CH02021.
(21) Matsuzaki, K.; Tahara, H.; Inokoshi, J.; Tanaka, H.; Masuma, R.; Omura, S. New brominated and halogen-less derivatives and structure-activity relationship of azaphilones inhibiting gp120-cd4 binding. *J. Antibiot.* 1998, 51, 1004-1011. https://doi.org/10.7164/antibiotics.51.1004.
(22) Arai, N.; Shiomi, K.; Tomoda, H.; Tabata, N.; Yang, D. J.; Masuma, R.; Kawakubo, T.; Omura, S. Isochromophilones III-VI, Inhibitors of acyl-coa: cholesterol acyltransferase produced by *penicillium* multicolor fo-3216. *J. Antibiot.* 1995, 48, 696-702. https://doi.org/10.7164/antibiotics.48.696.

(23) Frisvad, J. C.; Smedsgaard, J.; Larsen, T. O.; Samson, R. A. Mycotoxins, drugs and other extrolites produced by species in *Penicillium* subgenus *Penicillium*. *Stud. Mycol.*, 2004, 49, 201-241.
(24) Birkinshaw, J. H.; Kalyanpur, M. G.; Stickings, C. E. Studies in the biochemistry of microorganisms. 113. pencolide, a nitrogen-containing metabolite of *penicillium multicolor* grigorieva-manilova and poradielova. *Biochem. J.* 1963, 86, 237-243.
(25) Lucas, E. M. F.; Castro, M. C. M. de; Takahashi, J. A. Antimicrobial properties of sclerotiorin, isochromophilone VI and pencolide, metabolites from a brazilian cerrado isolate of *Penicillium sclerotiorum* van beyma. *Braz. J. Microbiol.* 2007, 38, 785-789. https://doi.org/10.1590/S1517-83822007000400036.
(26) Wang, X.; Sena Filho, J. G.; Hoover, A. R.; King, J. B.; Ellis, T. K.; Powell, D. R.; Cichewicz, R. H. Chemical epigenetics alters the secondary metabolite composition of guttate excreted by an atlantic-forest-soil-derived *Penicillium citreonigrum*. *J Nat. Prod.* 2010, 73, 942-948. https://doi.org/10.1021/np100142h.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:
1. A method of treating an infection with a *Mycobacterium* in a subject comprising administering to the subject a therapeutically effective amount of a compound of Formula IX

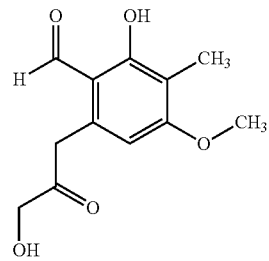

or a pharmaceutically acceptable salt thereof.
2. The method of claim 1, wherein the compound or pharmaceutically acceptable salt thereof is administered in combination with a pharmaceutically acceptable carrier to form a pharmaceutical composition.
3. The method of claim 1, wherein the infection comprises tuberculosis.
4. The method of claim 1, wherein the infection is caused by *Mycobacterium africanum*, *Mycobacterium bovis*, *Mycobacterium canetti*, *Mycobacterium caprae*, *Mycobacterium microti*, *Mycobacterium mungi*, *Mycobacterium orygis*, *Mycobacterium pinnipedii*, *Mycobacterium suricattae*, or *Mycobacterium tuberculosis*.
5. The method of claim 1, wherein the infection comprises leprosy.
6. The method of claim 1, wherein the infection is caused by *Mycobacterium leprae* or *Mycobacterium lepromatosis*.
7. The method of claim 1, wherein the infection is caused by *Mycobacterium avium*, *Mycobacterium avium paratuberculosis*, *Mycobacterium avium silvaticum*, *Mycobacterium avium hominissuis*, *Mycobacterium colombiense*, *Mycobacterium indicus pranii*, *Mycobacterium intracellulare*, *Mycobacterium ulcerans*, *Mycobacterium marinum*, *Mycobacterium kansasii*, *Mycobacterium abscessus*, *Mycobacterium chelonae*, *Mycobacterium fortuitum*, *mycobacterium terrae*, *Mycobacterium xenopi*, and *Mycobacterium simiae*.
8. The method of claim 1, wherein the compound is administered in combination or alternation with an additional therapeutic agent selected from ethambutol, isoniazid, pyrazinamide, rifampicin, streptomycin, acedapsone, clofazimine, dapsone, desoxyfructo-serotonin, ethionamide, rifapentine, sulfameter, thalidomide, or combinations thereof.
9. A method for killing one or more *Mycobacterium* cells comprising administering to the one or more *Mycobacterium* cells an effective amount of a compound of Formula IX

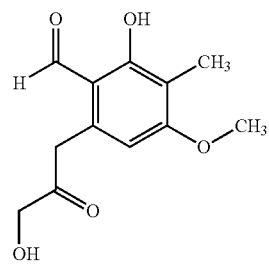

or a pharmaceutically acceptable salt thereof.
10. A method for inhibiting the growth of one or more *Mycobacterium* cells comprising administering to the one or more *Mycobacterium* cells an effective amount of a compound of Formula IX

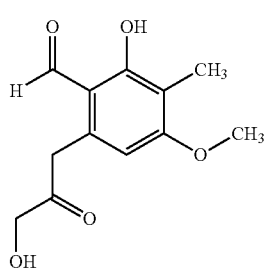
(IX)
or a pharmaceutically acceptable salt thereof.
* * * * *